United States Patent [19]

Küber et al.

[11] Patent Number: 5,693,730

[45] Date of Patent: Dec. 2, 1997

[54] METALLOCENES, PROCESS FOR THEIR PREPARATION AND THEIR USE AS CATALYSTS

[75] Inventors: Frank Küber, Oberursel; Michael Aulbach, Hofheim; Bernd Bachmann, Eppstein; Walter Spaleck, Liederbach; Andreas Winter, Glashütten, all of Germany

[73] Assignee: Hoechst Aktiengesellschaft, Germany

[21] Appl. No.: 473,079

[22] Filed: Jun. 7, 1995

Related U.S. Application Data

[62] Division of Ser. No. 344,730, Nov. 23, 1994, Pat. No. 5,585,508.

[30] Foreign Application Priority Data

| Nov. 24, 1993 | [DE] | Germany | 43 40 018.3 |
| Dec. 27, 1993 | [DE] | Germany | 43 44 708.2 |
| Dec. 27, 1993 | [DE] | Germany | 43 44 687.6 |

[51] Int. Cl.⁶ ............................................. C08F 4/64
[52] U.S. Cl. .................. 526/127; 526/153; 526/160; 526/351; 526/281; 526/282; 526/904; 526/943; 502/155
[58] Field of Search ................................ 526/127, 153, 526/160, 943, 904

[56] References Cited

U.S. PATENT DOCUMENTS

| 5,243,001 | 9/1993 | Winter et al. . |
| 5,278,264 | 1/1994 | Spaleck et al. . |
| 5,328,969 | 7/1994 | Winter et al. ................ 526/127 |
| 5,329,033 | 7/1994 | Spaleck et al. ............... 556/53 |
| 5,372,980 | 12/1994 | Davis ........................... 502/103 |
| 5,391,789 | 2/1995 | Rohrmann . |
| 5,416,178 | 5/1995 | Winter et al. . |
| 5,439,994 | 8/1995 | Inoue et al. ................... 526/114 |
| 5,455,366 | 10/1995 | Rohrmann et al. . |

FOREIGN PATENT DOCUMENTS

| 0 302 424 | 2/1989 | European Pat. Off. . |
| 0 485 822 | 5/1992 | European Pat. Off. . |
| 0 528 041 | 2/1993 | European Pat. Off. . |
| 0 528 287 | 2/1993 | European Pat. Off. . |
| 0 530 647 | 3/1993 | European Pat. Off. . |
| 0 545 303 | 6/1993 | European Pat. Off. . |
| 0 549 900 | 7/1993 | European Pat. Off. . |
| 0 578 838 | 1/1994 | European Pat. Off. . |
| 0 632 063 | 1/1995 | European Pat. Off. . |

OTHER PUBLICATIONS

Chemical Abstracts, vol. 117, No. 17, Abstract No. 171698x, "Preparation of Transition Metal Compounds as Catalysts for Polymerization", Oct., 1992.

Chemical Abstracts, vol. 117, No. 12, Abstract No. 112257e, "Preparation of Syndiotactic Polyolefins", Sep., 1992.

Chemical Abstracts, vol. 117, No. 10, Abstract No. 91047u, "Syndiotactic Polypropylene Prepared with Metallocene Catalysts", Sep., 1992.

*Primary Examiner*—David W. Wu
*Attorney, Agent, or Firm*—Connolly & Hutz

[57] ABSTRACT

The present invention relates to a polynuclear metallocene compound of the formula I

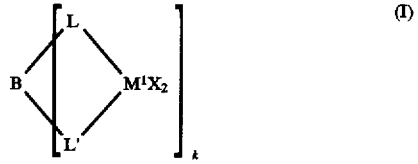

(I)

a process for their preparation and their use as a catalyst for olefin polymerization.

24 Claims, No Drawings

METALLOCENES, PROCESS FOR THEIR PREPARATION AND THEIR USE AS CATALYSTS

This application is a divisional of application Ser. No. 08/344,730 filed Nov. 23, 1994 now U.S. Pat. No. 5,585,508.

The present invention relates to novel metallocenes which contain more than one central atom and can be advantageously used as catalyst components in the preparation of polyolefins, in particular those having high stereoregularity, high molecular weight and good grain morphology.

The preparation of polyolefins using soluble metallocene compounds in combination with aluminoxanes or other cocatalysts, which owing to their Lewis acidity can convert the neutral metallocene into a cation and stabilize it, is known from the literature.

Soluble metallocene compounds based on bis(cyclopentadienyl)zirconium dialkyl or dihalide in combination with oligomeric aluminoxanes have good activity in polymerizing ethylene and moderate activity in polymerizing propylene. The polyethylene obtained has a narrow molecular weight distribution and intermediate molecular weight. The polypropylene prepared in this way is atactic and has a very low molecular weight.

The preparation of isotactic polypropylene can be successfully carried out using ethylene bis(4,5,6,7-tetra-hydro-1-indenyl)zirconium dichloride together with an aluminoxane in a suspension polymerization (EP 185 918). The polymer has a narrow molecular weight distribution. The disadvantage of this process is that at industrially applicable polymerization temperatures, only polymers having a very low molecular weight can be prepared.

There has also been described a specific preactivation method for the metallocene using an aluminoxane, which leads to an appreciable increase in the activity of the catalyst system and to a significant improvement in the grain morphology of the polymer (EP 302 424). However, the preactivation does not significantly increase the molecular weight.

Furthermore, catalysts based on ethylenebisindenyl-hafnium dichloride and ethylenebis(4,5,6,7-tetrahydro-1-indenyl)-hafnium dichloride and methylaluminoxane are known, by means of which relatively high-molecular-weight polypropylenes can be prepared by suspension polymerization (J. Am. Chem. Soc. (1987), 109, 6544). However, under industrially applicable polymerization conditions, the grain morphology of the polymers produced in this way is not satisfactory and the activity of the catalyst systems used is comparatively low. Furthermore, these systems have high catalyst costs, so that low-cost polymerization is not possible using these systems.

A significant increase in the molecular weight could be achieved by the use of metallocenes in which the indenyl ligands fixed by means of a bridge bear substituents in the 2 position (EP 485 822) or in the 2 and 4 positions (EP 530 647).

A further increase in the molecular weight was achieved by the use of indenyl ligands having substituents in the 2, 4 and 6 positions (EP 545 303) and also aromatic π ligands of the 4,5-benzoindenyl type (EP 549 900).

A disadvantage in the case of the stereospecific polymerization of prochiral monomers, e.g. of propylene, using metallocene catalysts is the relatively low isotacticity, which in the case of isotactic poly-propylene results in low melting points. Metallocenes having substituents in the 2 and 4 positions in particular and specifically rac-dimethylsilylbis (2-methyl-4-isopropylindenyl)zirconium dichloride in combination with methylaluminoxane give, in the case of propylene, a polymer having high isotacticity and therefore a high melting point (EP 530 647). A further increase in the melting points was achieved by the use of 4-aryl-substituted bisindenyl systems (EP 576 970). However, there are also industrial applications in which low melting points are desired.

A disadvantage of the use of soluble (homogeneous) metallocene-methylaluminoxane catalyst systems in processes in which the polymer is obtained as a solid, is the formation of heavy deposits on reactor walls and stirrers. These deposits are formed by agglomeration of the polymer particles if the metallocene or aluminoxane or both are present in solution in the suspension medium. Such deposits in the reactor systems have to be removed regularly, since these quickly reach considerable thicknesses, have a high strength and prevent heat exchange to the cooling medium.

To avoid reactor deposits, metallocenes can be supported. Processes for this purpose are known (EP 578 838). For technical reasons, it would be advantageous to omit the additional process step of supporting the catalyst. EP 528 041 discloses binuclear metallocenes which are suitable for the preparation of syndiotactic polymers having a low molecular weight.

It is an object of the invention to avoid the disadvantages of the prior art, and particularly to find a catalyst system which gives high yields of polymers having a very high molecular weight and, in the case of the stereo-specific polymerization of prochiral monomers, polymers having high stereoregularity.

It has now been found that metallocenes which contain more than one central atom and have a special bridge structure are suitable catalysts which avoid the disadvantages known from the prior art. Surprisingly, it has been further found that the metallocenes of the invention are particularly suitable for preparing isotactic polyolefins having only a low proportion of extractable material.

The present invention accordingly provides a polynuclear metallocene compound of the formula I

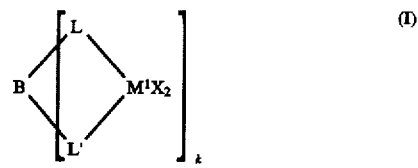

where

M¹ are identical or different and are a metal of group IVb, Vb or VIb of the Periodic Table, X are identical or different and are hydrogen, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-aryl-alkenyl group, an OH group, a halogen atom or pseudohalogen, L and L' are identical or different and are a π ligand or another electron donor, k is 2 if B is

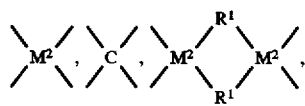

-continued

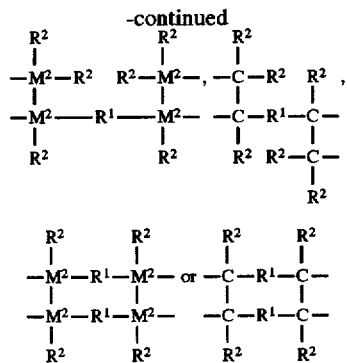

and k is an integer ≥2 if B is

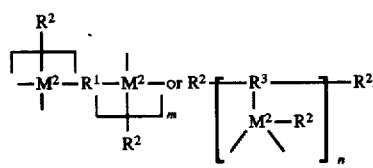

where $R^1$ are identical or different and are a divalent hydrocarbon-containing bridge structure, the radicals $R^2$ are identical or different and are a hydrogen atom, a halogen atom or a hydrocarbon-containing radical, $R^3$ is a trivalent hydrocarbon-containing radical, and n is k and m is k−1 and $M^2$ is silicon, germanium or tin.

For the purposes of clarity, it should be pointed out that each "free" valence of the structural elements B links to a ligand L or L'.

$M^1$ are identical or different and are a metal of the group IVb, Vb or VIb of the Periodic Table, for example titanium, zirconium, hafnium, vanadium, niobium, tantalum, chromium, molybdenum or tungsten, preferably zirconium, hafnium and titanium.

The radicals X are identical or different and are a hydrogen atom, a $C_1$–$C_{10}$-, preferably $C_1$–$C_4$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{12}$-alkylaryl group, a $C_8$–$C_{40}$-, preferably $C_8$–$C_{12}$-arylalkenyl group, or a halogen atom, preferably chlorine or a pseudohalgen like nitrile.

L and L' are identical or different and are preferably a substituted or unsubstituted cyclopentadienyl group, O, S, $PR^4$ or $NR^4$, where $R^4$ is a hydrogen atom or a $C_1$–$C_{30}$-hydrocarbon radical such as $C_1$–$C_{20}$-alkyl or $C_6$–$C_{14}$-aryl.

Examples of L and L' are:
tert-butylamido, cyclohexylamido, phenylamido, 2,6-diisopropylphenylamido, 2,6-ditert-butylphenylamido, cyclododecylamido, cyclopentadienyl, tetramethylcyclopentadienyl, methylcyclopentadienyl, methyl-tert-butylcyclopentadienyl, tert-butylcyclopenta-dienyl, isopropylcyclopentadienyl, dimethylcyclopentadienyl, trimethylcyclopentadienyl, trimethylethylcyclopentadienyl, phenylcyclopentadienyl, diphenylcyclopentadienyl, indenyl, 2-methylindenyl, 2-ethylindenyl, 3-methylindenyl, 3-tert-butylindenyl, 3-trimethylsilylindenyl, 2-methyl-4-phenylindenyl, 2-ethyl-4-phenylindenyl, 2-methyl-4-naphthylindenyl, 2-methyl-4-isopropylindenyl, 4,5-benzoindenyl, 2-methyl-4, 5-benzoindenyl, 2-methyl-α-acenaphthindenyl, 2-methyl-4,6-diisopropyl-indenyl, fluorenyl, 4-methylfluorenyl or 2,7-di-tert-butylfluorenyl.

B is

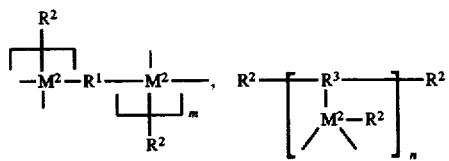

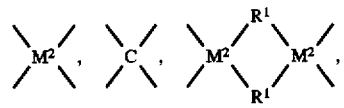

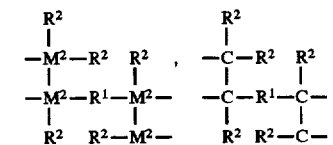

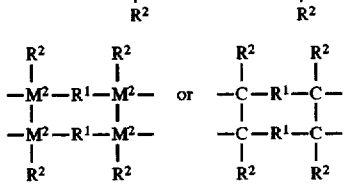

where $R^1$ are identical or different and are a divalent hydrocarbon-containing $C_1$–$C_{40}$ bridge structure, preferably a divalent $C_1$–$C_{40}$-alkyl group, $C_1$–$C_{10}$-fluoroalkyl group, $C_6$–$C_{10}$-aryl group, $C_6$–$C_{10}$-fluoroaryl group, $C_7$–$C_{20}$-alkylaryl group, $C_7$–$C_{20}$-arylalkyl group, $C_1$–$C_{10}$-alkoxy group, $C_6$–$C_{10}$-aryloxy group, $C_2$–$C_{10}$-alkenyl group or $C_8$–$C_{20}$-arylalkenyl group, the radicals $R^2$ are identical or different and are a hydrogen atom, a halogen atom, or a hydrocarbon-containing $C_1$–$C_{40}$ radical such as a $C_1$–$C_{10}$-alkyl group, a $C_1$–$C_{10}$-fluoroalkyl group, a $C_1$–$C_{10}$-alkoxy group, a $C_6$–$C_{10}$-aryl group, a $C_6$–$C_{10}$-fluoroaryl group, a $C_6$–$C_{10}$-aryloxy group, a $C_2$–$C_{10}$-alkenyl group, a $C_7$–$C_{20}$-alkylaryl group, a $C_7$–$C_{40}$-alkylaryl group or a $C_8$–$C_{40}$-arylalkenyl group and $R^3$ is a trivalent hydrocarbon-containing $C_1$–$C_{40}$ radical, preferably a $C_1$–$C_{40}$-hydrocarbon radical, particularly preferably a trivalent $C_7$–$C_{40}$-alkyl group, $C_1$–$C_{40}$-alkylaryl group, $C_6$–$C_{40}$-arylalkyl group, $C_2$–$C_{40}$-alkenyl group or $C_8$–$C_{40}$-arylalkenyl group, n is k and m is k−1 and $M^2$ is silicon, germanium or tin.

If B is

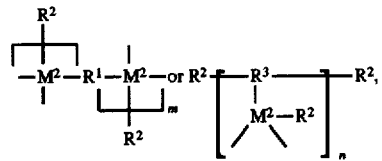

k is preferably an integer from 2 to 100,000, particularly preferably from 2 to 20, in particular 2.

Preferably, B is

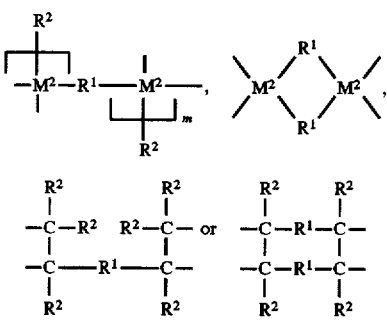

where the radicals $R^1$ are identical or different and are a divalent $C_1$–$C_{10}$-, preferably $C_1$–$C_6$-alkyl group which can be linear or branched, in particular 1,2-ethanediyl, 1,3-propanediyl, 1,4-butanediyl, 1,6-hexanediyl, ethylene, 1,3-propylene, 1,4-butylene, 1,6-hexylene, a $C_6$–$C_{10}$-, preferably $C_6$-aryl group, in particular 1,4-phenylene, a $C_6$–$C_{10}$-fluoroaryl, preferably $C_6$-fluoroaryl group, a $C_7$–$C_{20}$-alkylaryl, preferably $C_7$–$C_{12}$-alkyl-aryl group, in particular p-xylylene, m-xylylene, o-xylylene, a $C_7$–$C_{20}$-arylalkyl, preferably $C_7$–$C_{12}$-arylalkyl group, a $C_1$–$C_{10}$-alkoxy, preferably $C_1$–$C_6$-alkoxy group, a $C_2$–$C_{10}$-alkenyl, preferably $C_2$–$C_6$-alkenyl group, a $C_8$–$C_{20}$-arylalkenyl, preferably $C_8$–$C_{14}$-arylalkenyl group, the radicals $R^2$ are identical or different and are a hydrogen atom, a halogen atom, a $C_1$–$C_{10}$-, preferably $C_1$–$C_4$-alkyl group, in particular a methyl group, a $C_1$–$C_{10}$-fluoroalkyl, preferably $CF_3$ group, a $C_6$–$C_{20}$-, preferably $C_6$–$C_{10}$-aryl group, a $C_6$–$C_{10}$-fluoroaryl group, preferably a pentafluorophenyl group, a $C_1$–$C_{10}$-, preferably $C_1$–$C_4$-alkoxy group, in particular a methoxy group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group, a $C_7$–$C_{40}$-, preferably $C_7$–$C_{12}$-alkylaryl group, and n is k and m is k–1, and $M^2$ is silicon, germanium or tin, preferably silicon or germanium, in particular silicon.

Preference is given to compounds of the formula II

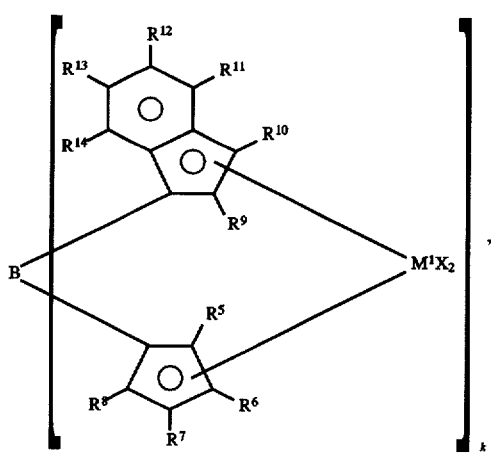

formula II where $M^1$ are identical or different and are a metal of group IVb, Vb or VIb of the Periodic Table, X are identical or different and are hydrogen, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-aryl-alkenyl group, an OH group, a halogen atom or pseudo-halogen, the radicals $R^5$, $R^6$, $R^7$ and $R^8$ are identical or different and are a hydrogen atom, a halogen atom, a $C_1$–$C_{10}$-alkyl group which can be halogenated, a $C_6$–$C_{20}$-aryl group, a $C_7$–$C_{40}$-arylalkyl group, a $C_7$–$C_{20}$-alkylaryl group, a $C_2$–$C_{10}$-alkenyl group, a $C_8$–$C_{40}$-arylalkenyl group, a $-NR^{15}_2$, $-SR^{15}$, $-OSiR^{15}_3$, $-SiR^{15}_3$ or $-PR^{15}_2$ radical, where $R^{15}$ is identical or different and is a $C_1$–$C_{10}$-alkyl group or a $C_6$–$C_{10}$-aryl group, or two or more adjacent radicals $R^5$, $R^6$, $R^7$ and $R^8$ together with the atoms connecting them form a ring system, $R^9$ to $R^{14}$ are identical or different and are a hydrogen atom, a halogen atom, a $C_1$–$C_{10}$-alkyl group which can be halogenated, a $C_6$–$C_{20}$-aryl group, a $C_7$–$C_{40}$-arylalkyl group, a $C_7$–$C_{40}$-alkylaryl group, a $C_2$–$C_{10}$-alkenyl group, a $C_8$–$C_{40}$-arylalkenyl group, a $-NR^{15}_2$, $-SR^{15}$, $-OSiR^{15}_3$, $-SiR^{15}_3$ or $-PR^{15}_2$ radical, where $R^{15}$ is identical or different and is a $C_1$–$C_{10}$-alkyl group or a $C_6$–$C_{10}$-aryl group, or two or more adjacent radicals $R^9$, $R^{10}$, $R^{11}$, $R^{12}$, $R^{13}$ and $R^{14}$ together with the atoms connecting them form a ring system, k is 2, if B is

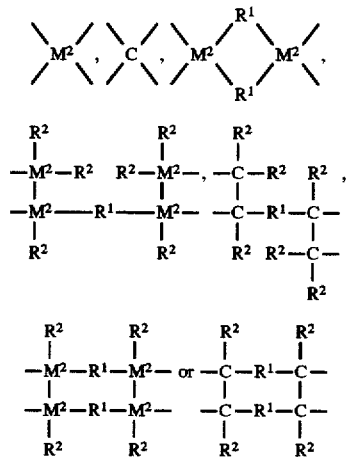

and k is an integer $\geq 2$, if B is

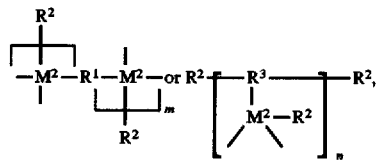

where $R^1$ are identical or different and are a divalent hydrocarbon-containing $C_1$–$C_{40}$ bridge structure, the radicals $R^2$ are identical or different and are a hydrogen atom, a halogen atom or a hydrocarbon-containing $C_1$–$C_{40}$ radical, $R^3$ is a trivalent hydrocarbon-containing $C_1$–$C_{40}$ radical, and n is k and m is k–1 and $M^2$ is silicon, germanium or tin.

For compounds of the formula II, it is particularly preferred that $M^1$ are identical or different and are zirconium or hafnium, the radicals X are identical and are a $C_1$–$C_4$-alkyl group, a $C_7$–$C_{10}$-alkylaryl group or a halogen atom, $R^5$ to $R^8$ are identical or different and are a hydrogen atom, a $C_1$–$C_{10}$-alkyl group, a $C_6$–$C_{20}$-aryl group or a $SiR^{15}_3$ radical, where $R^{15}$ is a $C_1$–$C_{10}$-alkyl group, or the radicals $R^5$ and $R^6$ and/or $R^7$ and $R^8$ together with the atoms connecting them form an aromatic or aliphatic ring system, $R^9$ to $R^{14}$ are identical or different and are a hydrogen atom, a $C_1$–$C_{10}$-alkyl group or a $C_6$–$C_{20}$-aryl group, or $R^9$ and $R^{10}$ and/or two or more adjacent radicals $R^{11}$, $R^{12}$, $R^{13}$ and $R^{14}$ together with the atoms connecting them form an aromatic or aliphatic ring system, k is 2, B is

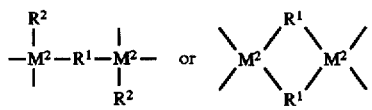

where $M^2$ is silicon, $R^1$ are identical or different and are a divalent linear or branched $C_1$–$C_6$-alkyl group, in particular 1,2-ethylene, 1,3-propylene, 1,4-butylene or 1,6-hexylene and the radicals $R^2$ are identical or different and are hydrogen, a $C_1$–$C_4$-alkyl group or a $C_6$–$C_{10}$-aryl group.

Isotactic polyolefins are preferably prepared using compounds of the formula II which have two indenyl groups as ligands. For this purpose, particular preference is given to compounds of the formula II in which the indenyl groups are substituted in the 2 position, 2,4 positions, 2,6 positions, 2,4,6 positions, 2,4,5 positions, 2,4,5,6 positions and 2,5,6 positions, with the 2 position preferably being substituted by a $C_1$–$C_{10}$-alkyl radical and the 4, 5 and 6 positions being substituted by $C_1$–$C_{10}$-alkyl radicals, $C_6$–$C_{10}$-aryl radicals or by fusion in the 4,5 or 4,5,6 positions. The term ring system thus includes both substituted and unsubstituted ring systems.

The nomenclature used for the point of substitution is as follows:

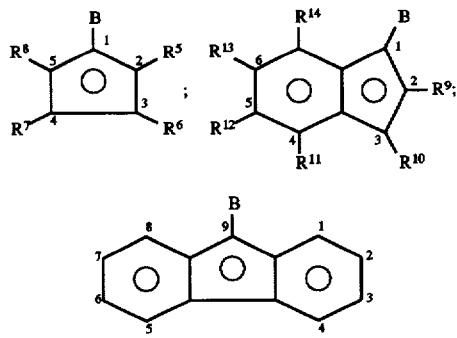

Preferred ligands are:

1-indenyl, 2-alkyl-4-aryl-1-indenyl, 2,4-dialkyl-1-indenyl, 2,4-diaryl-1-indenyl, 2,4,6-trialkyl-1-indenyl, 1-alkyl-α-acenaphth-1-indenyl, 1-alkyl-4,5-benzo-1-indenyl, 2,5-dialkyl-1-indenyl, 2,5,6-trialkyl-1-indenyl, 2,4,5-trialkyl-1-indenyl, 2-alkyl-1-indenyl, 2-aryl-1-indenyl, 2,6-dialkyl-4-aryl-1-indenyl, 2-alkyl-5-aryl-1indenyl, 2-alkyl-5,6-diaryl-1-indenyl, 2-alkyl-4,5-diaryl-1-indenyl, 2-alkyl-4,6-diaryl-1-indenyl, fluorenyl, 2,7-dialkylfluorenyl, or 4-alkylfluorenyl, 2-alkyl-1-cyclopentadienyl, 2,4-dialkyl-1-cyclopentadienyl, 2,4,5-trialkyl-1-cyclopentadienyl, 2-Si(trialkyl)-1-cyclopentadienyl, 2-Si(trialkyl)-4-alkyl-1-cyclopentadienyl, 2-Si(trialkyl)-4,5-dialkyl-1-cyclopentadienyl, 2-alkyl-4-aryl-1-cyclopentadienyl, 2,5-alkyl-4-aryl-1-cyclopentadienyl, 2,4-alkyl-5-aryl-1-cyclopentadienyl, 2-aryl-1-cyclopentadienyl, 2-aryl-4-alkyl-1-cyclopentadienyl, 2-aryl-4,5-alkyl-1-cyclopenta-dienyl or 2-alkyl-4,5-aryl-1-cyclopentadienyl.

The following examples are intended to illustrate in more detail the compounds described by the formula I. However, the list is not claimed to be complete:

1,6-bis[methylsilyl(fluorenyl)(cyclopentadienyl)zirconium dichloride)]hexane, 1,6-bis[methylsilyl(indenyl)(cyclopentadienyl)zirconium dichloride]hexane, 1,6-bis[methylsilyl(fluorenyl)(3-methylcyclopentadienyl) zirconium dichloride]hexane, 1,6-bis[methylsilyl(indenyl)(3-methylcyclopentadienyl) zirconium dichloride]hexane, 1,6-bis[methylsilyl-(fluorenyl)(3-isopropylcyclopentadienyl)zirconium dichloride]hexane, 1,6-bis[methylsilyl-(indenyl)(3-isopropylcyclopentadienyl) zirconium dichloride]hexane, 1,6-bis[methylsilyl-(2,7-di-tert-butylfluorenyl) (cyclopentadienyl)zirconium dichloride]hexane, 1,6-bis[methylsilyl-(2-methylindenyl)(cyclopentadienyl) zirconium dichloride]hexane, 1,6-bis[methylsilyl-(2-methyl-4-phenylindenyl) (cyclopentadienyl)zirconium dichloride]hexane, 1,6-bis[methylsilyl-(4-phenylindenyl)(cyclopentadienyl)-zirconium dichloride]hexane, 1,6-bis[methylsilyl-(2-methyl-4-phenylindenyl)(2,3,5-trimethylcyclopentadienyl)zirconium dichloride]hexane, 1,6-bis[methylsilyl-(indenyl)3-phenylcyclopentadienyl)-zirconium dichloride]hexane, 1,6-bis[methylsilyl-(2-methyl-4,5-benzoindenyl) (cyclopentadienyl)zirconium dichloride]hexane, 1,6-bis[methylsilyl-(2-methyl-4,6-diisopropylindenyl) (cyclopentadienyl)zirconium dichloride]hexane, 1,6-bis[methylsilyl-(2-methyl-4-(1-naphthylindenyl)-(cyclopentadienyl)zirconium dichloride]hexane, 1,6-bis[methylsilyl-(2-ethyl-4-phenylindenyl) (cyclopentadienyl)zirconium dichloride]hexane, 1,6-bis[methylsilyl-(2-methyl-4,5-benzoindenyl)(2,3,5-trimethylcyclopentadienyl)zirconium dichloride]hexane, 1,6-bis[methylsilyl-(2-methyl-4,6-diisopropylindenyl)(2,3, 5-trimethylclopentadienyl)zirconium dichloride]hexane, 1,6- bis[methylsilyl-(2-methyl-4-(1-naphthylindenyl)-(2,3, 5-trimethylcyclopentadienyl)zirconium dichloride] hexane, 1,6-bis[methylsilyl-(2-ethyl-4-phenylindenyl)(2,3,5-trimethylcyclopentadienyl)zirconium dichloride]hexane, 1,2-bis[methylsilyl-(fluorenyl)(cyclopentadienyl)-zirconium dichloride]ethane, 1,2-bis[methylsilyl-(indenyl)(cyclopentadienyl)zirconium dichloride]ethane, 1,2-bis[methylsilyl-(fluorenyl)(3-methylcyclopenta-dienyl) zirconium dichloride]ethane, 1,2-bis[methylsilyl-(indenyl)(3-methylcyclopentadienyl)-zirconium dichloride]ethane, 1,2-bis[methylsilyl-(fluorenyl)(3-isopropylcyclopentadienyl)zirconium dichloride]ethane, 1,2-bis[methylsilyl-(indenyl)(3-isopropylcyclopentadienyl) zirconium dichloride]ethane, 1,2-bis[methylsilyl-(2,7-di-tert-butylfluorenyl) (cyclopentadienyl)zirconium dichloride]ethane, 1,2-bis[methylsilyl-(2-methylindenyl)(cyclopentadienyl)-zirconium dichloride]ethane, 1,2-bis[methylsilyl-(2-methyl-4-phenylindenyl)(cyclopentadienyl)zirconium dichloride]ethane, 1,2-bis[methylsilyl-(4-phenylindenyl)(cyclopentadienyl)zirconium dichloride]ethane, 1,2-bis[methylsilyl-(2-methyl-4-phenylindenyl)(2,3,5-trimethylcyclopentadienyl)zirconium dichloride]ethane, 1,2-bis[methylsilyl-(fluorenyl)(3-phenylcyclopentadienyl)zirconium dichloride]ethane, 1,2-bis[methylsilyl-(indenyl)(3-phenylcyclopentadienyl)zirconium dichloride]ethane, 1,2 -bis[methylsilyl-(2-methyl-4,5-benzoindenyl)(cyclopentadienyl)zirconium dichloride]ethane, 1,2-bis[methylsilyl-(2-methyl-4,6-diisopropylindenyl)(cyclopentadienyl)zirconium dichloride]ethane, 1,2-bis[methylsilyl-(2-methyl-4-(1-naphthylindenyl)(cyclopentadienyl)zirconium dichloride]ethane, 1,2-bis[methylsilyl-(2-ethyl-4-phenylindenyl)(cyclopentadienyl)zirconium dichloride]ethane, 1,2-bis[methylsilyl-(2-methyl-4,5-benzoindenyl)(2,3,5-trimethylcyclopentadienyl)zirconium dichloride]ethane, 1,2-bis[methylsilyl-(2-methyl-4,6-diisopropylindenyl)(2,3,5-trimethylcyclopentadienyl)zirconium dichloride]ethane, 1,2-bis[methylsilyl-(2-methyl-4-(1-naphthylindenyl)(2,3,5-trimethylcyclopentadienyl)zirconium dichloride]ethane, 1,2-bis[methylsilyl-(2-ethyl-4-phenylindenyl)(2,3,5-trimethylcyclopentadienyl)zirconium dichloride]ethane, 1,4-disilacyclohexane-1,4-diylidene[(fluorenyl)(cyclopentadienyl)zirconium dichloride], 1,4-disilacyclohexane-1,4-diylidene[(indenyl)(cyclopentadienyl)zirconium dichloride], 1,4-disilacyclohexane-1,4-diylidene[(fluorenyl)(3-methylcyclopentadienyl)zirconium dichloride], 1,4-disilacyclohexane-1,4-diylidene[(indenyl)(3-methylcyclopentadienyl)zirconium dichloride], 1,4-disilacyclohexane-1,4-diylidene[(fluorenyl)(3-isopropylcyclopentadienyl)zirconium dichloride], 1,4-disilacyclohexane-1,4-diylidene[(indenyl)(3-isopropylcyciopentadienyl)zirconium dichloride], 1,4-disilacyclohexane-1,4-diylidene[(2,7-di-tert-butyl-fluorenyl)(cyclopentadienyl)zirconium dichloride], 1,4-disilacyclohexane-1,4-diylidene[(2-methylindenyl)-(cyclopentadienyl)zirconium dichloride], 1,4-disilacyclohexane-1,4-diylidene[(2-methyl-4-phenylindenyl)(cyclopentadienyl)zirconium dichloride], 1,4-disilacyclohexane-1,4-diylidene[(4-phenylindenyl)-(cyclopentadienyl)zirconium dichloride], 1,4-disilacyclohexane-1,4-diylidene[(2-methyl-4-phenylindenyl)(2,3,5-trimethylcyclopentadienyl)zirconium dichloride], 1,4-disilacyclohexane-1,4-diylidene[(fluorenyl)(3-phenylcyclopentadienyl)zirconium dichloride], 1,4-disilacyclohexane-1,4-diylidene[(indenyl)(3-phenylcyclopentadienyl)zirconium dichloride], 1,4-disilacyclohexane-1,4-diylidene[(2-methyl-4,5-benzoindenyl)(cyclopentadienyl)zirconium dichloride], 1,4-disilacyclohexane-1,4-diylidene[(2-methyl-4,6-diisopropylindenyl)(cyclopentadienyl)zirconium dichloride], 1,4-disilacyclohexane-1,4-diylidene[(2-methyl-4-(1-napthylindenyl)(cyclopentadienyl)zirconium dichloride], 1,4-disilacyclohexane-1,4-diylidene[(2-ethyl-4-phenylindenyl)(cyclopentadienyl)zirconium dichloride], 1,4-disilacyclohexane-1,4-diylidene[(2-methyl-4,5 -benzoindenyl)(2,3,5-trimethylcyclopentadienyl)zirconium dichloride], 1,4-disilacyclohexane-1,4-diylidene[(2-methyl-4,6-diisopropylindenyl)(2,3,5-trimethylcyclopentadienyl)zirconium dichloride], 1,4-disilacyclohexane-1,4-diylidene[(2-methyl-4-(1-naphthylindenyl)(2,3,5-trimethylcyclopentadienyl)-zirconium dichloride], 1,4-disilacyclohexane-1,4-diylidene[(2-ethyl-4-phenyl-indenyl)(2,3,5-trimethylcyclopentadienyl)zirconium dichloride], 9,10-dihydro-9,10-disilaanthracene-9,10-diylidene-[(fluorenyl)(cyclopentadienyl)zirconium dichloride], 9,10-dihydro-9,10-disilaanthracene-9,10-diylidene-[(indenyl)(cyclopentadienyl)zirconium dichloride], 9,10-dihydro-9,10-disilaanthracene-9,10-diylidene-[(fluorenyl)(3-methylcyclopentadienyl)zirconium dichloride], 9,10-dihydro-9,10-disilaanthracene-9,10-diylidene[(indenyl)(3-methylcyclopentadienyl)zirconium dichloride], 9,10-dihydro-9,10-disilaanthracene-9,10-diylidene-[(fluorenyl)(3-isopropylcyclopentadienyl)zirconium dichloride], 9,10-dihydro-9,10-disilaanthracene-9,10-diylidene-[(indenyl)(3-isopropylcyclopentadienyl)zirconium dichloride], 9,10-dihydro-9,10-disilaanthracene-9,10-diylidene[(2,7-di-tert-butylfluorenyl)(cyclopentadienyl)zirconium dichloride], 9,10dihydro-9,10-disilaanthracene-9,10-diylidene[(2-methylindenyl)(cyclopentadienyl)zirconium dichloride], 9,10-dihydro-9,10-disilaanthracene-9,10-diylidene[(2-methyl-4-phenylindenyl)(cyclopentadienyl)zirconium dichloride], 9,10-dihydro-9,10-disilaanthracene-9,10-diylidene[(4-phenylindenyl)(cyclopentadienyl)zirconium dichloride], 9,10-dihydro-9,10-disilaanthracene-9,10-diylidene[(2-methyl-4-phenylindenyl)(2,3,5-trimethylcyclopentadienyl)-zirconium dichloride], 9,10-dihydro-9,10-disilaanthracene-9,10-diylidene[(fluorenyl)(3-phenylcyclopentadienyl)zirconium dichloride], 9,10-dihydro-9,10-disilaanthracene-9,10-diylidene[(indenyl)(3-phenylcyclopentadienyl)zirconium dichloride], 9,10-dihydro-9,10-disilaanthracene-9,10-diylidene[(2-methyl-4,5-benzoindenyl)(cyclopentadienyl)zirconium dichloride], 9,10-dihydro-9,10-disilaanthracene-9,10-diylidene[(2-methyl-4,6-diisopropylindenyl)(cyclopentadienyl)zirconium dichloride], 9,10-dihydro-9,10-disilaanthracene-9,10-diylidene[(2-methyl-4-(1-naphthylindenyl)(cyclopentadienyl)zirconium dichloride], 9,10-dihydro-9,10-disilaanthracene-9,10-diylidene[(2-ethyl-4-phenylindenyl)(cyclopentadienyl)zirconium dichloride], 9,10-dihydro-9,10-disilaanthracene-9,10-diylidene[(2-methyl-4,5-benzoindenyl)(2,3,5-trimethylcyclopentadienyl)zirconium dichloride], 9,10-dihydro-9,10-disilaanthracene-9,10-diylidene[(2-methyl-4,6-diisopropylindenyl)(2,3,5-trimethylcyclopentadienyl)zirconium dichloride], 9,10-dihydro-9,10-disilaanthracene-9,10-diylidene[(2-methyl-4(1-naphthylindenyl)(2,3,5-trimethylcyclopentadienyl)zirconium dichloride], 9,10-dihydro-9,10-disilaanthracene-9,10-diylidene[(2-ethyl-4-phenylindenyl)(2,3,5-trimethylcyclopentadienyl)-zirconium dichloride], 1,6-bis[methylsilyl-bis(indenyl)zirconium dichloride] hexane, 1,6-bis[methylsilyl-bis(2-methylindenyl)zirconium dichloride]hexane,
1,6-bis[methylsilyl-bis(2-methyl-4-phenylindenyl) zirconium dichloride]hexane,
1,6-bis[methylsilyl-bis(2-methyl-4,5-benzoindenyl) zirconium dichloride]hexane,
1,6-bis[methylsilyl-bis(2-methyl-4-(1-naphthyl)indenyl)- zirconium dichloride]hexane,
1,6-bis[methylsilyl-bis(2-methyl-4-isopropylindenyl) zirconium dichloride]hexane,
1,6-bis[methylsilyl-bis(2-methyl-4,6-diisopropylindenyl)- zirconium dichloride]hexane,
1,6-bis[methylsilyl-bis(2-ethylindenyl)zirconium dichloride]hexane,
1,6-bis[methylsilyl-bis(2-ethyl-4-phenylindenyl)-zirconium dichloride]hexane,
1,6-bis[methylsilyl-bis(2-ethyl-4-(1-naphthyl)indenyl)- zirconium dichloride]hexane,
1,6-bis[methylsilyl-bis(2-ethyl-α-acenaphthindenyl)- zirconium dichloride]hexane,
1,2-bis[methylsilyl-bis(indenyl)zirconium dichloride] ethane,
1,2-bis[methylsilyl-bis(2-methylindenyl)zirconium dichloride]ethane,
1,2-bis[methylsilyl-bis(2-methyl-4-phenylindenyl) zirconium dichloride]ethane,
1,2-bis[methylsilyl-bis(2-methyl-4,5-benzoindenyl)- zirconium dichloride]ethane,
1,2-bis[methylsilyl-bis(2-methyl-4-(1-naphthyl)indenyl)- zirconium dichloride]ethane,
1,2-bis[methylsilyl-bis(2-methyl-4-isopropylindenyl)- zirconium dichloride]ethane,
1,2-bis[methylsilyl-bis(2-methyl-4,6-diisopropylindenyl)- zirconium dichloride]ethane,
1,2-bis[methylsilyl-bis(2-ethylindenyl)zirconium dichloride]ethane,
1,2-bis[methylsilyl-bis(2-ethyl-4-phenylindenyl)-zirconium dichloride]ethane,
1,2-bis[methylsilyl-bis(2-ethyl-4-(1-naphthyl)indenyl)- zirconium dichloride]ethane,
1,2-bis[methylsilyl-bis(2-ethyl-α-acenaphthindenyl)- zirconium dichloride]ethane,
1,2-bis[methylsilyl-bis(indenyl)zirconium dichloride] ethane,
1,2-bis[methylsilyl-bis(2-methylindenyl)zirconium dichloride]ethane,
1,2-bis[ethylsilyl-bis(2-methyl-4-phenylindenyl)-zirconium dichloride]ethane,
1,2-bis[ethylsilyl-bis(2-methyl-4,5-benzoindenyl)- zirconium dichloride]ethane,
1,2-bis[ethylsilyl-bis(2-methyl-4-(1-naphthyl)indenyl)- zirconium dichloride]ethane,
1,2-bis[ethylsilyl-bis(2-methyl-4-isopropylindenyl)- zirconium dichloride]ethane,
1,2-bis[ethylsilyl-bis(2-methyl-4,6-diisopropylindenyl)- zirconium dichloride]ethane,
1,2-bis[ethylsilyl-bis(2-ethylindenyl)zirconium dichloride] ethane,
1,2-bis[ethylsilyl-bis(2-ethyl-4-phenylindenyl)zirconium dichloride]ethane,
1,2-bis[ethylsilyl-bis(2-ethyl-4-(1-naphthyl)indenyl)- zirconium dichloride]ethane,
1,2-bis[ethylsilyl-bis(2-ethyl-α-acenaphthindenyl)- zirconium dichloride]ethane,
1,6-bis[ethylsilyl-bis(indenyl)zirconium dichloride]hexane,
1,6-bis[ethylsilyl-bis(2-methylindenyl)zirconium dichloride]hexane,
1,6-bis[ethylsilyl-bis(2-methyl-4-phenylindenyl)zirconium dichloride]hexane,
1,6-bis[ethylsilyl-bis(2-methyl-4,5-benzoindenyl)zirconium dichloride]hexane,
1,6-bis[ethylsilyl-bis(2-methyl-4-(1-naphthyl)indenyl)- zirconium dichloride]hexane,
1,6-bis[ethylsilyl-bis(2-methyl-4-isopropylindenyl) zirconium dichloride]hexane,
1,6-bis[ethylsilyl-bis(2-methyl-4,6-diisopropylindenyl) zirconium dichloride]hexane.
1,6-bis[ethylsilyl-bis(2-ethylindenyl)zirconium dichloride] hexane,
1,6-bis[ethylsilyl-bis(2-ethyl-4-phenylindenyl)zirconium dichloride]hexane,
1,6-bis[ethylsilyl-bis(2-ethyl-4-(1-naphthyl)indenyl) zirconium dichloride]hexane,
1,6-bis[ethylsilyl-bis(2-ethyl-α-acenaphthindenyl) zirconium dichloride]hexane,
1,3-bis[methylsilyl-bis(indenyl)zirconium dichloride]- propane,
1,3-bis[methylsilyl-bis(2-methylindenyl)zirconium dichloride]propane,
1,3-bis[methylsilyl-bis(2-methyl-4-phenylindenyl) zirconium dichloride]propane,
1,3-bis[methylsilyl-bis(2-methyl-4,5-benzoindenyl) zirconium dichloride]propane,
1,3-bis[methylsilyl-bis(2-methyl-4-(1-naphthyl)indenyl)- zirconium dichloride]propane,
1,3-bis[methylsilyl-bis(2-methyl-4-isopropylindenyl) zirconium dichloride]propane,
1,3-bis[methylsilyl-bis(2-methyl-4,6-diisopropylindenyl)- zirconium dichloride]propane,
1,3-bis[methylsilyl-bis(2-ethylindenyl)zirconium dichloride]propane,
1,3-bis[methylsilyl-bis(2-ethyl-4-phenylindenyl)zirconium dichloride]propane,
1,3-bis[methylsilyl-bis(2-ethyl-4-(1-naphthyl)indenyl) zirconium dichloride]propane,
1,3-bis[methylsilyl-bis(2-ethyl-α-acenaphthindenyl) zirconium dichloride]propane,
1,4-disilacyclohexane-1,4-diylidene[bis(indenyl)zirconium dichloride],
1,4-disilacyclohexane-1,4-diylidene[bis(2-methylindenyl) zirconium dichloride],
1,4-disilacyclohexane-1,4-diylidene[bis(2-ethylindenyl) zirconium dichloride],
1,4-disilacyclohexane-1,4-diylidene[bis(2-methyl-4-phenylindenyl)zirconium dichloride],
1,4-disilacyclohexane-1,4-diylidene[bis(2-methyl-4-(1-naphthylindenyl)zirconium dichloride],
1,4-disilacyclohexane-1,4-diylidene[bis(2-methyl-4-isopropylindenyl)zirconium dichloride],
1,4-disilacyclohexane-1,4-diylidene[bis(2-methyl-4,6-diisopropylindenyl)zirconium dichloride],
1,4-disilacyclohexane-1,4-diylidene[bis(2-methyl-4,5-benzoindenyl)zirconium dichloride],
1,4-disilacyclohexane-1,4-diylidene[bis(2-ethyl-4-phenylindenyl)zirconium dichloride],
1,4-disilacyclohexane-1,4-diylidene[bis(2-methyl-α-acenaphthindenyl)zirconium dichloride],
9,10-dihydro-9,10-disilaanthracene-9,10-diylidene[bis (indenyl)zirconium dichloride],
9,10-dihydro-9,10-disilaanthracene-9,10-diylidene[bis(2-methylindenyl)zirconium dichloride],
9,10-dihydro-9,10-disilaanthracene-9,10-diylidene[bis(2-ethylindenyl)zirconium dichloride],
9,10-dihydro-9,10-disilaanthracene-9,10-diylidene[bis(2-methyl-4-phenylindenyl)zirconium dichloride], 9,10-dihydro-9,10-disilaanthracene-9,10-diylidene[bis(2-methyl-4-(1-naphthylindenyl)zirconium dichloride],
9,10-dihydro-9,10-disilaanthracene-9,10-diylidene[bis(2-methyl-4-isopropylindenyl)zirconium dichloride],
9,10-dihydro-9,10-disilaanthracene-9,10-diylidene[bis(2-methyl-4,6-diisopropylindenyl)zirconium dichloride],
9,10-dihydro-9,10-disilaanthracene-9,10-diylidene[bis(2-methyl-4,5-benzoindenyl)zirconium dichloride],
9,10-dihydro-9,10-disilaanthracene-9,10-diylidene[bis(2-ethyl-4-phenylindenyl)zirconium dichloride],
9,10-dihydro-9,10-disilaanthracene-9,10-diylidene[bis(2-methyl-α-acenaphthindenyl)zirconium dichloride],
1,4-dihydro-1,4-disilabenzene-1,4-diylidene[bis(indenyl)zirconium dichloride],
1,4-dihydro-1,4-disilabenzene-1,4-diylidene[bis(2-methylindenyl)zirconium dichloride],
1,4-dihydro-1,4-disilabenzene-1,4-diylidene[bis(2-ethylindenyl)zirconium dichloride],
1,4-dihydro-1,4-disilabenzene-1,4-diylidene[bis(2-methyl-4-phenylindenyl)zirconium dichloride],
1,4-dihydro-1,4-disilabenzene-1,4-diylidene[bis(2-methyl-4-(1-naphthylindenyl)zirconium dichloride],
1,4-dihydro-1,4-disilabenzene-1,4-diylidene[bis(2-methyl-4-isopropylindenyl)zirconium dichloride],
1,4-dihydro-1,4-disilabenzene-1,4-diylidene[bis(2-methyl-4,6-diisopropylindenyl)zirconium dichloride],
1,4-dihydro-1,4-disilabenzene-1,4-diylidene[bis(2-methyl-4,5-benzoindenyl)zirconium dichloride],
1,4-dihydro-1,4-disilabenzene-1,4-diylidene[bis(2-ethyl-4-phenylindenyl)zirconium dichloride],
1,4-dihydro-1,4-disilabenzene-1,4-diylidene[bis(2-methyl-α-acenaphthindenyl)zirconium dichloride],
1,4-dihydro-1,4-disila-2,3,5,6-tetraphenylbenzene-1,4-diylidene[bis(indenyl)zirconium dichloride],
1,4-dihydro-1,4-disila-2,3,5,6-tetraphenylbenzene-1,4-diylidene[bis(2-methylindenyl)zirconium dichloride],
1,4-dihydro-1,4-disila-2,3,5,6-tetraphenylbenzene-1,4-diylidene[bis(2-ethylindenyl)zirconium dichloride],
1,4-dihydro-1,4-disila-2,3,5,6-tetraphenylbenzene-1,4-diylidene[bis(2-methyl-4-phenylindenyl)zirconium dichloride],
1,4-dihydro-1,4-disila-2,3,5,6-tetraphenylbenzene-1,4-diylidene[bis(2-methyl-4-(1-naphthylindenyl)zirconium dichloride],
1,4-dihydro-1,4-disila-2,3,5,6-tetraphenylbenzene-1,4-diylidene[bis(2-methyl-4-isopropylindenyl)zirconium dichloride],
1,4-dihydro-1,4-disila-2,3,5,6-tetraphenylbenzene-1,4-diylidene[bis(2-methyl-4,6-diisopropylindenyl)zirconium dichloride],
1,4-dihydro-1,4-disila-2,3,5,6-tetraphenylbenzene-1,4-diylidene[bis(2-methyl-4,5-benzoindenyl)zirconium dichloride],
1,4-dihydro-1,4-disila-2,3,5,6-tetraphenylbenzene-1,4-diylidene[bis(2-ethyl-4-phenylindenyl)zirconium dichloride],
1,4-dihydro-1,4-disila-2,3,5,6-tetraphenylbenzene-1,4-diylidene[bis(2-methyl-α-acenaphthindenyl)zirconium dichloride],
1,6-bis[methylsilyl-(2-methyl-4-phenylindenyl)(2-methylindenyl)zirconium dichloride]hexane,
1,6-bis[methylsilyl-(2-methyl-4-phenylindenyl)(indenyl)zirconium dichloride]hexane,
1,6-bis[methylsilyl-(2-methyl-4-phenylindenyl)(2-methyl-4,5-benzoindenyl)zirconium dichloride]hexane,
1,6-bis[methylsilyl-(2-methyl-4-phenylindenyl)(2-methyl-4-(1-naphthyl)indenyl)zirconium dichloride]hexane,
1,6-bis[methylsilyl-(2-methyl-4-phenylindenyl)(2-methyl-4-isopropylindenyl)zirconium dichloride]hexane,
1,6-bis[methylsilyl-(2-methyl-4-phenylindenyl)(2-methyl-4,6-diisopropylindenyl)zirconium dichloride]hexane,
1,6-bis[methylsilyl-(2-methyl-4-phenylindenyl)(2-ethylindenyl)zirconium dichloride]hexane,
1,6-bis[methylsilyl-(2-methyl-4-phenylindenyl)(2-ethyl-4-phenylindenyl)zirconium dichloride]hexane,
1,6-bis[methylsilyl-(2-methyl-4-phenylindenyl)(2-methyl-α-acenaphthindenyl)zirconium dichloride]hexane,
1,2-bis[methylsilyl-(2-methyl-4-phenylindenyl)(indenyl)zirconium dichloride]ethane,
1,2-bis[methylsilyl-(2-methyl-4-phenylindenyl)(2-methylindenyl)zirconium dichloride]ethane,
1,2-bis[methylsilyl-(2-methyl-4-phenylindenyl)(2-methyl-4,5-benzoindenyl)zirconium dichloride]ethane,
1,2-bis[methylsilyl-(2-methyl-4-phenylindenyl)(2-methyl-4,5-benzoindenyl)zirconium dichloride]ethane,
1,2-bis[methylsilyl-(2-methyl-4-phenylindenyl)(2-methyl-4-(1-naphthyl)indenyl)zirconium dichloride]ethane,
1,2-bis[methylsilyl-(2-methyl-4-phenylindenyl)(2-methyl-4-isopropylindenyl)zirconium dichloride]ethane,
1,2-bis[methylsilyl-(2-methyl-4-phenylindenyl)(2-methyl-4,6-diisopropylindenyl)zirconium dichloride]ethane,
1,2-bis[methylsilyl-(2-methyl-4-phenylindenyl)(2-ethylindenyl)zirconium dichloride]ethane,
1,2-bis[methylsilyl-(2-methyl-4-phenylindenyl)(2-ethyl-4-phenylindenyl)zirconium dichloride]ethane,
1,2-bis[methylsilyl-(2-methyl-4-phenylindenyl)(2-ethyl-4-(1-naphthyl)indenyl)zirconium dichloride]ethane,
1,2-bis[methylsilyl-(2-methyl-4-phenylindenyl)(2-methyl-α-acenaphthindenyl)zirconium dichloride]ethane,
1,4-disilacyclohexane-1,4-diylidene[(2-methyl-4-phenylindenyl)(indenyl)zirconium dichloride],
1,4-disilacyclohexane-1,4-diylidene[(2-methyl-4-phenylindenyl)(2-methylindenyl)zirconium dichloride],
1,4-disilacyclohexane-1,4-diylidene[(2-methyl-4-phenylindenyl)(2-ethylindenyl)zirconium dichloride],
1,4-disilacyclohexane-1,4-diylidene[(2-methyl-4-phenylindenyl)(2-methyl-4-(1-naphthylindenyl)zirconium dichloride],
1,4-disilacyclohexane-1,4-diylidene[(2-methyl-4-phenylindenyl)(2-methyl-4-isopropylindenyl)zirconium dichloride],
1,4-disilacyclohexane-1,4-diylidene[(2-methyl-4-phenylindenyl)(2-methyl-4,6-diisopropylindenyl)zirconium dichloride],
1,4-disilacyclohexane-1,4-diylidene[(2-methyl-4-phenylindenyl)(2-methyl-4,5-benzoindenyl)zirconium dichloride],
1,4-disilacyclohexane-1,4-diylidene[(2-methyl-4-phenylindenyl(2-ethyl-4-phenylindenyl)zirconium dichloride],
1,4-disilacyclohexane-1,4-diylidene[(2-methyl-4-phenylindenyl)(2-methyl-α-methylacenaphthindenyl)zirconium dichloride],
9,10-dihydro-9,10-disilaanthracene-9,10-diylidene[(2-methyl-4-phenylindenyl)(indenyl)zirconium dichloride],
9,10-dihydro-9,10-disilaanthracene-9,10-diylidene[(2-methyl-4-phenylindenyl)(2-methylindenyl)zirconium dichloride],
9,10-dihydro-9,10-disilaanthracene-9,10-diylidene[(2-methyl-4-phenylindenyl)(2-ethylindenyl)zirconium dichloride],
9,10-dihydro-9,10-disilaanthracene-9,10-diylidene[(2-methyl-4-phenylindenyl)(2-methyl-4-isopropylindenyl)zirconium dichloride], 9,10-dihydro-9,10-disilaanthracene-9,10-diylidene[(2-methyl-4-phenylindenyl)(2-methyl-4,6-diisopropylindenyl)zirconium dichloride], 9,10-dihydro-9,10-disilaanthracene-9,10-diylidene[(2-methyl-4-phenylindenyl)(2-methyl-4,5-benzoindenyl)zirconium dichloride], 9,10-dihydro-9,10-disilaanthracene-9,10-diylidene[(2-methyl-4-phenylindenyl)(2-ethyl-4-phenylindenyl)zirconium dichloride], 9,10-dihydro-9,10-disilaanthracene-9,10-diylidene[(2-methyl-4-phenylindenyl)(2-methyl-α-acenaphthindenyl)zirconium dichloride], 1,4-dihydro-1,4-disilabenzene-1,4-diylidene[(2-methyl-4-phenylindenyl)(indenyl)zirconium dichloride], 1,4-dihydro-1,4-disilabenzene-1,4-diylidene[(2-methyl-4-phenylindenyl)(2-methylindenyl)zirconium dichloride], 1,4-dihydro-1,4-disilabenzene-1,4-diylidene[(2-methyl-4-phenylindenyl)(2-ethylindenyl)zirconium dichloride], 1,4-dihydro-1,4-disilabenzene-1,4-diylidene[(2-methyl-4-phenylindenyl)(2-methyl-4-(1-naphthylindenyl)zirconium dichloride], 1,4-dihydro-1,4-disilabenzene-1,4-diylidene[(2-methyl-4-phenylindenyl)(2-methyl-4-isopropylindenyl)zirconium dichloride], 1,4-dihydro-1,4-disilabenzene-1,4-diylidene[(2-methyl-4-phenylindenyl)(2-methyl-4,6-diisopropylindenyl)zirconium dichloride], 1,4-dihydro-1,4-disilabenzene-1,4-diylidene[(2-methyl-4-phenylindenyl)(2-methyl-4,5-benzoindenyl)zirconium dichloride], 1,4-dihydro-1,4-disilabenzene-1,4-diylidene[(2-methyl-4-phenylindenyl)(2-ethyl-4-phenylindenyl)zirconium dichloride] and 1,4-dihydro-1,4-disilabenzene-1,4-diylidene[(2-methyl-4-phenylindenyl)(2-methyl-α-acenaphthindenyl)zirconium dichloride].

The preparation of the metallocenes of the invention is illustrated by the following reaction scheme.

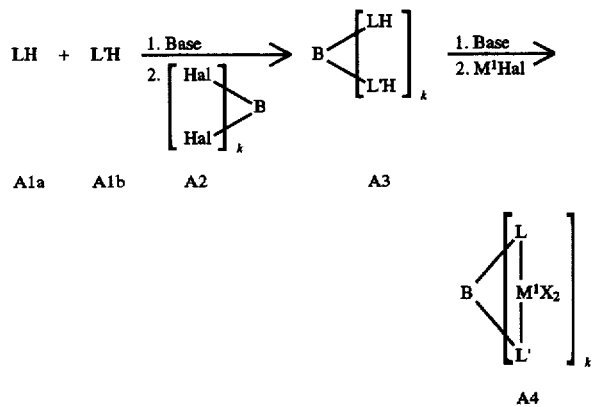

If desired, radicals X which are not halogen can be introduced into the metallocene A4, for example by reaction with alkylating agents such as methyllithium, to obtain metallocenes of the formula I in which X is not halogen.

The indene derivatives are commercially available or can be prepared by methods known in the literature (EP 567 952, EP 545 304).

The processes for preparing the ligand systems and the reaction to give the bridged metallocenes of the formula I is known in principle (EP 574 597, EP 320 762, EP 376 154).

For this purpose, LH and L'H are deprotonated with a strong base, such as, for example, butyllithium or potassium hydride, in an inert solvent and reacted with a reagent of the formula A2 to give the ligand system of the formula A3 or one of its isomers, with the double bond in the five-membered ring being able to lie either between C(2) and C(3) or between C(1) and C(2). The ligand system is subsequently deprotonated with 2 k equivalents of a strong base such as, for example, butyllithium or potassium hydride in an inert solvent and reacted with k equivalents of a metal tetrahalide such as, for example, zirconium tetrachloride in a suitable solvent to give A4. Suitable solvents are aliphatic or aromatic solvents such as, for example, hexane or toluene, etheric solvents such as, for example, tetrahydrofuran or diethyl ether or halogenated hydrocarbons such as, for example, methylene chloride or halogenated aromatic hydrocarbons such as, for example, o-dichlorobenzene. It is also possible to use a mixture of a plurality of metal halides, for example zirconium tetrachloride and hafnium tetrachloride. In this way, polynuclear metallocenes which bear various metals in one molecule are obtained.

The present invention also provides a process for preparing an olefin polymer by polymerization of at least one olefin in the presence of a catalyst containing at least one polynuclear metallocene and at least one cocatalyst, wherein the polynuclear metallocene is a compound of the formula I.

The polymerization can be a homopolymerization or a copolymerization. Preferably, olefins of the formula $R^a$—CH=CH—$R^b$ are homopolymerized or copolymerized, where $R^a$ and $R^b$ are identical or different and are a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, dienes such as 1,3-butadiene or 1,4-hexadiene and cyclic olefins such as norbornene, tetracyclododecene, norbornadiene or vinyl-norbornene.

In the process of the invention, preference is given to homopolymerizing ethylene or propylene, or copolymerizing ethylene with one or more 1-olefins having 3–20 carbon atoms, such as propylene, and/or one or more dienes having 4–20 carbon atoms, such as 1,3-butadiene. Examples of copolymers are ethylene/propylene copolymers and ethylene/propylene/1,4-hexadiene copolymers, ethylene/propylene/5-ethylidene-2-norbornene-copolymers and ethylene-norbornene-copolymers.

The catalyst used in the process of the invention preferably comprises a polynuclear metallocene of the formula I and a cocatalyst. It is also possible to use mixtures of the polynuclear metallocenes of the invention with mononuclear metallocenes. In principle, the cocatalyst in the process of the invention can be any compound which, owing to its Lewis acidity, can convert the neutral metallocene into a cation and stabilize it ("labile coordination"). Furthermore, the cocatalyst or the anion formed therefrom should undergo no further reactions with the metallocene cation formed (EP 427 697). The cocatalyst used is preferably an aluminum compound and/or a boron compound.

The boron compound preferably has the formula $R^{16}_x NH_{4-x} BR^{17}_4$, $R^{16}_x PH_{4-x} BR^{17}_4$, $R^{16}_3 CBR^{17}_4$ or $BR^{17}_3$, where x is a number from 1 to 4, preferably 3, the radicals $R^{16}$ are identical or different, preferably identical, and are $C_1$-$C_{10}$-alkyl or $C_6$-$C_{18}$-aryl, or two radicals $R^{16}$ together with the atoms connecting them form a ring, and the radicals $R^{17}$ are identical or different, preferably identical, and are $C_6$-$C_{18}$-aryl which can be substituted by alkyl, haloalkyl or fluorine. In particular, $R^{16}$ is ethyl, propyl, butyl or phenyl and $R^{17}$ is phenyl, pentafluorophenyl, 3,5- bistrifluoromethylphenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular an aluminoxane of the formula IIIa for the linear type and/or the formula IIIb for the cyclic type,

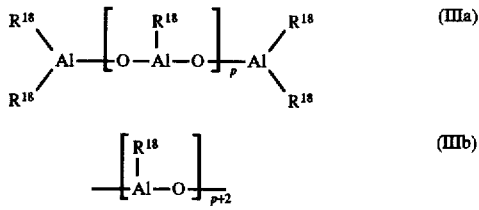

where in the formulae IIIa and IIIb, the radicals $R^{18}$ can be identical or different and are a $C_1$–$C_6$-alkyl group, a $C_6$–$C_{18}$-aryl group, benzyl or hydrogen, and p is an integer from 2 to 50, preferably from 10 to 35.

The radicals $R^{18}$ are preferably identical and are methyl, isobutyl, phenyl or benzyl, particularly preferably methyl.

If the radicals $R^{18}$ are different, they are preferably methyl and hydrogen or alternatively methyl and isobutyl, with hydrogen or isobutyl preferably being present in an amount of from 0.01 to 40% (number of the radicals $R^{18}$).

The processes for preparing the aluminoxanes are known.

Regardless of the method of preparation, all aluminoxane solutions have in common a varying content of unreacted aluminum starting compound, which is present in free form or as an adduct.

It is possible to preactivate the metallocene prior to use in the polymerization reaction using an aluminoxane of the formula IIIa and/or IIIb. This significantly increases the polymerization activity and improves the grain morphology. The preactivation of the transition metal compound is carried out in solution. Preferably, the metallocene is here dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of $10^{-4}$–1 mol per mole of aluminoxane. The preactivation takes from 5 minutes to 60 hours, preferably from 5 to 60 minutes. It is carried out at a temperature of from –78° to 100° C., preferably from 0° to 70° C.

A prepolymerization can be carried out with the aid of the metallocene. For the prepolymerization, preference is given to using the (or one of the) olefin(s) used in the polymerization.

To control the grain morphology, the metallocene can also be applied to a support. Suitable support materials are, for example, silica gels, aluminum oxides, solid aluminoxane or other inorganic support materials such as, for example, magnesium chloride. Polyolefin powder in finely divided form is also a suitable support material. The preparation of the supported catalyst can be carried out, for example, as described in EP 578 838.

When using the abovementioned cocatalysts, the actual (active) polymerization catalyst is the reaction product of metallocene and one of the specified compounds. For this reason, this reaction product is preferably first prepared outside the polymerization reactor in a separate step using a suitable solvent.

To remove catalyst poisons present in the olefin, purification using an aluminum alkyl, for example trimethylaluminum or triethylaluminum is advantageous. This purification can either be carried out in the polymerization system itself, or the olefin is, prior to addition to the polymerization system, brought into contact with the aluminum compound and is subsequently separated off again.

The polymerization is carried out in a known manner in solution, in suspension or in the gas phase, continuously or batchwise, in one or more stages at a temperature of from –60° to 250° C., preferably from 30° to 100° C., particularly preferably from 50° to 80° C.

As molecular weight regulator and/or to increase the activity, hydrogen is added if necessary. The total pressure in the polymerization system is from 0.5 to 100 bar. Preference is given to polymerization in the pressure range from 5 to 64 bar, which is particularly important in industry.

In this polymerization, the metallocene is used in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is used in a concentration of from $10^{-5}$ to $10^{-1}$ mol, preferably from $10^{-4}$ to $10^{-2}$ mol, per $dm^3$ of solvent or per $dm^3$ of reactor volume. The other specified cocatalysts are used in approximately equimolar amounts to the metallocene, in principle however, higher concentrations are also possible.

If the polymerization is carried out as suspension or solution polymerization, an inert solvent customary for the Ziegler low-pressure process is used. For example, it is carried out in an aliphatic or cycloaliphatic hydrocarbon; examples of such which may be mentioned are propane, butane, hexane, heptane, isooctane, cyclohexane, methylcyclohexane. Furthermore, a gasoline or hydrogenated diesel oil fraction can be employed. It is also possible to use toluene. Preferably, polymerization is carried out in the liquid monomer.

If inert solvents are used, the monomers are metered in in gaseous or liquid form.

The duration of polymerization can be any desired, since the catalyst system to be used according to the invention shows only a low time-dependent fall in the polymerization activity.

The polymers prepared by the process of the invention are suitable for the production of semi-finished parts and extruded shaped parts such as films, sheets or large hollow bodies (e.g. pipes). With appropriate selection of the monomers, it is also possible to prepare rubbers or elastomers.

In the process of the invention, the metallocenes described produce, in the temperature range from 50° to 80° C. which is of particular importance in industry and at high catalyst activities, polymers having a very high molecular weight, in the case of prochiral monomers very high molecular weight and very high stereotacticity. In addition, a complicated isomer separation can be omitted for the metallocene synthesis.

In particular, in the case of the stereospecific polymerization of prochiral olefins, for example of propylene, the metallocene of the invention gives polymers having high stereoregularity and molecular weight. Particularly in the case of the isospecific polymerization of propylene, it gives isotactic polypropylene having high isotactic sequence lengths and a high melting point.

If the metallocene of the invention has different types of central atoms, polyolefins having a broad, bimodal or polymodal molecular weight distribution are obtained.

Furthermore, reactor deposits can be avoided using the metallocene of the invention, without the catalyst having to be supported.

In addition, the metallocene of the invention is suitable for preparing ethylene-containing copolymers such as rubbers or elastomers having a high proportion of comonomer and particularly regular incorporation of comonomer.

The following examples illustrate the invention in more detail.

All glass apparatus was baked out in vacuo and flushed with argon. All operations were carried out with exclusion of moisture and oxygen in Schlenk vessels. The solvents used were in each case freshly distilled under argon over Na/K alloy and stored in Schlenk vessels.

The Al/CH$_3$ ratio in the aluminoxane was determined by decomposition of the sample with H$_2$SO$_4$ and determination of the volume of the hydrolysis gases formed under standard conditions and also by complexometric titration of the aluminum in the then dissolved sample by the Schwarzenbach method.

Toluene-soluble methylaluminoxane was used as a 10% strength by weight toluene solution for the examples of suspension polymerization and of bulk polymerization using unsupported metallocene and contained 36 mg Al/cm$^3$, according to the aluminum determination. The mean degree of oligomerization according to freezing point depression in benzene was n=20. For the toluene-soluble methylaluminoxane, an Al:CH$_3$ ratio of 1:1.55 was found.

DEFINITONS

VN=viscosity number in cm$^3$/g
M$_w$=weight average molecular weight in g/mol (determined by gel permeation chromatography)
M$_w$/M$_n$=polydispersity
Mp.=melting point in °C. (determined by DSC, 20° C./min heating/cooling rate)
II=isotactic index (II=mm+½ mr, determined by $^{13}$C-NMR spectroscopy)
MFI 230/5=melt flow index, measured in accordance with DIN 53735; in dg/min
BD=polymer bulk density in g/dm$^3$.

Synthesis of the metallocenes used in the polymerization examples (the starting materials used are commercially available):

A. 1,6-bis[methylsilyl-bis(2-methyl-4-phenylindenyl)-zirconium dichloride]hexane (1)

36.1 ml (97 mmol) of a 20% strength solution of butyllithium in toluene were added dropwise at room temperature over a period of 30 minutes to a solution of 20 g (97 mmol) of 2-methyl-7-phenylindene in 200 ml of O$_2$-free and H$_2$O-free toleuene and 10 ml of oxygen-free anhydrous THF under an argon atmosphere. After addition was complete, the mixture was heated for a further 2 hours at 80° C. Subsequently, 7.6 g (24.3 mmol) of 1,6-bis(methyldichlorosilyl)hexane in 10 ml of toluene were added dropwise at from 0° to 5° C. over a period of 30 minutes and the mixture was stirred for a further 1.5 hours at room temperature. For the workup, 100 ml of water were adddes, the phases were separated and the organic phase was freed of solvent. After filtration through 200 g of silica gel (hexane/CH$_2$Cl$_2$ 5:1), 11.7 g (48%) of the ligand system were obtained as a viscous oil.

22 ml (59 mmol) of a 20% strength solution of butyllithium in toluene were added dropwise at room temperature under an argon atmosphere over a period of 30 minutes to a solution of 11.7 g (12 mmol) of ligand in 150 ml of oxygen-free anhydrous diethyl ether. After addition was complete, the mixture was heated under reflux for a further 2 hours, the solvent was removed in vacuo and the residue was filtered using hexane through a G3 Schlenk frit. The tetralithium salt was dried for a number of hours in an oil pump vacuum at room temperature and subsequently added at −78° C. to a suspension of 5.5 g (24 mmol) of zirconium tetrachloride in 200 ml of oxygen-free anhydrous CH$_2$Cl$_2$. The cooling bath was removed and the mixture was stirred for a further 1 hour at room temperature. The reaction mixture was filtered through a G3 Schlenk frit, the filtrate was freed of solvent in vacuo and the residue was washed a number of times with hexane. Subsequently, it was recrystallized from toluene at −30° C. This gave 7.3 g (47%) of 1 as isomer mixture in the form of a yellow amorphous solid.

$^1$H-NMR (100 MHz), CDCl$_3$): 6.8 to 7.8 (m, 36 H, arom. H and β-H-indene); 2.1 and 2.3 (2 m, 12 H, CH$_3$-indene); 1.2 to 2.0 (m, 18 H, 4CH$_2$, CH$_2$Si and CH$_3$Si). Mass spectrum: 1306 M$^+$, correct disintegration pattern.

B. 1,2-bis[methylsilyl-bis(2-methyl-4-phenylindenyl)-zirconium dichloride]ethane (2)

36.1 ml (97 mmol) of a 20% strength solution of butyllithium in toluene were added dropwise at room temperature over a period of 30 minutes to a solution of 20 g (97 mmol) of 2-methyl-7-phenylindene in 200 ml of oxygen-free anhydrous toluene and 10 ml of O$_2$-free and H$_2$O-free anhydrous THF under an argon atmosphere. After addition was complete, the mixture was heated for a further 2 hours at 80° C. Subsequently, 6.2 g (24.2 mmol) of 1,2-bis (methyldichlorosilyl)ethane in 10 ml of toluene were added dropwise at from 0° to 5° C. over a period of 30 minutes and the mixture was stirred for a further 1.5 hours at room temperature. For the workup, 100 ml of water were added, the phases were separated and the organic phase was freed of solvent. After filtration through 200 g of silica gel (hexane/CH$_2$Cl$_2$5:1), 11.8 g (52%) of the ligand system were obtained as a viscous oil.

21.5 ml (57.6 mmol) of a 20% strength solution of butyllithium in toluene were added dropwise at room temperature under an argon atmosphere over a period of 30 minutes to a solution of 10.8 g (11 mmol) of ligand in 150 ml of oxygen-free anhydrous diethyl ether. After addition was complete, the mixture was heated under reflux for a further 2 hours, the solvent was removed in vacuo and the residue was filtered using hexane through a G3 Schlenk frit. The tetralithium salt was dried for a number of hours in an oil pump vacuum at room temperature and subsequently added at −78° C. to a suspension of 5.4 g (23 mmol) of zirconium tetrachloride in 200 ml of oxygen-free anhydrous CH$_2$Cl$_2$. The cooling bath was removed and the mixture was stirred for a further 1 hour at room temperature. The reaction mixture was filtered through a G3 Schlenk frit, the filtrate was freed of solvent in vacuo and the residue was washed a number of times with hexane. Subsequently, it was recrystallized from toluene at −30° C. This gave 5.6 g (39%) of 2 as isomer mixture in the form of a yellow amorphous solid.

$^1$H-NMR (100 MHz), CDCl$_3$): 6.9 to 7.8 (m, 36 H, arom. H and β-H-indene); 2.3 and 2.5 (2 m, 12 H, CH$_3$-indene); 1.2 to 1.7 (m, 10 H, CH$_2$Si and CH$_3$Si). Mass spectrum: 1250 M$^+$, correct disintegration pattern.

C. 1,6-bis[methylsilyl-(2-methylindenyl)(2-methyl-4-phenylindenyl)zirconium dichloride]hexane (3)

27 ml (73 mmol) of a 20% strength solution of butyllithium in toluene were added dropwise at room temperature over a period of 30 minutes to a solution of 15 g (73 mmol) of 2-methyl-7-phenylindene in 150 ml of toluene and 10 ml of THF. After addition was complete, the mixture was heated for a further 2 hours at 80° C. Subsequently, 11.2 g (36 mmol) of 1,6-bis(methyldichlorosilyl)hexane in 10 ml of toluene were added dropwise at from 0° to 5° C. over a period of 2 minutes and the mixture was stirred for a further 1.5 hours at room temperature. The solvents were removed and the residue was taken up in toluene and precipitated LiCl was subsequently filtered off. A suspension of 2-methylindenyllithium (prepared by reaction of 9.5 g (73 mmol) of 2-methylindene in 100 ml of toluene and 20 ml of THF at room temperature with 27 ml (73 mmol) of a 20% strength solution of butyllithium in toluene and stirring further for 1 hour at 50° C.) was added dropwise at room temperature to the filtrate over a period of 30 minutes and the mixture was subsequently stirred for a further 2 hours at room temperature. The reaction mixture was admixed with 100 ml of water, the phases were separated and the organic phase was washed with 50 ml of water. The solvents were removed in vacuo and the residue was purified by chromatography on 500 g of silica gel (hexane/methylene chloride 1:1). This gave 7.3 g (24%) of the unsymmetric ligand system of compound 3 as a very viscous oil.

15 ml (40 mmol) of a 20% strength solution of butyllithium in toluene were added dropwise at room temperature over a period of 30 minutes to a solution of 7.1 g (8.4 mmol) of the ligand system of compound 3 in 50 ml of diethyl ether. After addition was complete, the mixture was heated under reflux for a further 2 hours, the solvent was removed in vacuo and the residue was filtered using hexane through a G3 Schlenk frit. The tetralithium salt was dried for a number of hours in an oil pump vacuum at room temperature and subsequently added at −78° C. to a suspension of 3.7 g (16 mmol) of zirconium tetrachloride in 50 ml of $O_2$-free and $H_2O$-free $CH_2Cl_2$. The cooling bath was removed and the mixture was stirred for a further 1 hour at room temperature. The reaction mixture was filtered through a G3 Schlenk frit, the residue was extracted further with a total of 200 ml of methylene chloride and the combined filtrates were largely freed of solvent in vacuo. The residue was washed a number of times with hexane/methylene chloride 1:1 and subsequently dried. This gave 4.2 g (43%) of compound 3 as a yellow amorphous solid.

$^1$H-NMR (100 MHz, $CDCl_3$): 6.7 to 8.0 (m, 28 H, arom. H and β-indH); 2.1 and 2.3 (2 m, 12 H, $CH_3$-indene); 1.2–2.0 (m, 18 H, $4CH_2$, $CH_2Si$ and $CH_3Si$).

D. 1,2-bis[methylsilyl-(indenyl)(2-methyl-4-phenyl-indenyl)zirconium dichloride]ethane (4)

27 ml (73 mmol) of a 20% strength solution of butyllithium in toluene were added dropwise at room temperature to a solution of 15 g (73 mmol) of 2-methyl-7-phenylindene in 150 ml of toluene and 8 ml of THF over a period of 30 minutes. After addition was complete, the mixture was heated to 80° C. for a further 2 hours. Subsequently, 11.2 g (36 mmol) of 1,2-bis(methyldichlorosilyl)ethane in 10 ml of toluene were added dropwise at from 0° to 5° C. over a period of 2 minutes and the mixture was stirred for a further 1.5 hours at room temperature. The solvents were removed and the residue was taken up in toluene and precipitated LiCl was subsequently filtered off. A suspension of indenyllithium (prepared by reacting 8.5 g (73 mmol) of indene in 100 ml of toluene and 20 ml of THF at room temperature with 27 ml (73 mmol) of a 20% strength solution of butyllithium in toluene and stirring further for 1 hour at 50° C.) was added dropwise at room temperature to the filtrate over a period of 30 minutes and the mixture was subsequently stirred for a further 2 hours at room temperature. The reaction mixture was admixed with 100 ml of water, the phases were separated and the organic phase was washed with 50 ml of water. The solvents were removed in vacuo and the residue was purified by chromatography on 500 g of silica gel (hexane/methylene chloride 1:1). This gave 9.3 g (31%) of the unsymmetric ligand system of compound 4 as a very viscous oil.

17 ml (46 mmol) of a 20% strength solution of butyllithium in toluene were added dropwise at room temperature to a solution of 9.1 g (11 mmol) of the ligand system of compound 4 in 150 ml of diethyl ether over a period of 30 minutes. After addition was complete, the mixture was heated under reflux for a further 2 hours, the solvent was removed in vacuo and the residue was filtered using hexane through a G3 Schlenk frit. The tetralithium salt was dried for a number of hours in an oil pump vacuum at room temperature and subsequently added at −78° C. to a suspension of 4.9 g (21 mmol) of zirconium tetrachloride in 200 ml of $CH_2Cl_2$. The cooling bath was removed and the mixture was stirred for a further 1 hour at room temperature. The reaction mixture was filtered through a G3 Schlenk frit, the residue was extracted further with a total of 400 ml of methylene chloride and the combined filtrates were largely freed of solvent in vacuo. The residue was washed a number of times with 10 ml of methylene chloride each time and was subsequently dried. This gave 4.3 g (34%) of compound 4 as a yellow amorphous solid.

$^1$H-NMR (100 MHz, $CDCl_3$): 6.9–7.8 (m, 28 H, arom. H and β-indH); 6.3 (m, 2H, α-indH), 2.4 (m, 6 H, $CH_3$-indene); 1.2–2.0 (m, 18 H, $4CH_2$, $CH_2Si$ and $CH_3Si$).

E. 1,6-bis[methylsilyl-(2,3,5-trimethylcyclopenta-dienyl)(2-methyl-4-phenylindenyl)zirconium dichloride]hexane (5)

27 ml (73 mmol) of a 20% strength solution of butyllithium in toluene were added dropwise at room temperature to a solution of 15 g (73 mmol) of 2-methyl-7-phenylindene in 150 ml of toluene and 8 ml of THF over a period of 30 minutes. After addition was complete, the mixture was heated for a further 2 hours at 80° C. Subsequently, 11.2 g (36 mmol) of 1,6-bis(methyldichlorosilyl)hexane in 10 ml of toluene were added dropwise at from 0° to 5° C. over a period of 2 minutes and the mixture was stirred for a further 1.5 hours at room temperature. The solvents were removed and the residue was taken up in toluene and precipitated LiCl was subsequently filtered off. A suspension of 1,2,4-trimethylcyclopentadienyllithium (prepared by reacting 7.9 g (73 mmol) of 1,2,4-trimethylcyclopentadiene in 100 ml of toluene and 20 ml of THF at room temperature with 27 ml (73 mmol) of a 20% strength solution of butyllithium in toluene and stirring for a further 1 hour at room temperature) was added dropwise at room temperature to the filtrate over a period of 30 minutes and the mixture was subsequently stirred for a further 2 hours at room temperature. The reaction mixture was admixed with 100 ml of water, the phases were separated and the organic phase was washed with 50 ml of water. The solvents were removed in vacuo and the residue was purified by chromatography on 700 g of silica gel (hexane/AcOEt 5:1). This gave 13.5 g (47%) of the ligand system of compound 5 as a very viscous oil.

26 ml (70 mmol) of a 20% strength solution of butyllithium in toluene were added dropwise at room temperature to a solution of 13 g (16.5 mmol) of the ligand system of compound 5 in 150 ml of diethyl ether over a period of 30 minutes. After addition was complete, the mixture was heated for a further 2 hours under reflux, the solvent was removed in vacuo and the residue was filtered using hexane through a G3 Schlenk frit. The tetralithium salt was dried for a number of hours in an oil pump vacuum at room temperature and subsequently added at −78° C. to a suspension of 7.5 g (32 mmol) of zirconium tetrachloride in 150 ml of $CH_2Cl_2$. The cooling bath was removed and the mixture was stirred for a further 1 hour at room temperature. The reaction mixture was filtered through a G3 Schlenk flit, the residue was extracted further with a total of 100 ml of methylene chloride and the combined filtrates were largely freed of solvent in vacuo. The residue was washed a number of times with hexane and subsequently dried. This gave 6.1 g (36%) of compound 5 as a yellow amorphous solid.

$^1$H-NMR (100 MHz, CDCl$_3$): 6.9 to 8.0 (m, 18 H, arom. H and β-indH); 6.4 (s, 1H, H-Cp), 1.9 to 2.2 (m, 24 H, CH$_3$-ind and -Cp); 1.2 to 2.0 (m, 18 H, 4CH$_2$, CH$_2$Si and CH$_3$Si).

F. 1,6-bis[methylsilyl-(3-isopropylcyclopentadienyl)-(fluorenyl)zirconium dichloride]hexane (6)

22 ml (60 mmol) of a 22% strength solution of butyl-lithium in toluene were added dropwise at room temperature to a solution of 10 g (60 mmol) of fluorene in 100 ml of toluene and 10 ml of diethyl ether over a period of 30 minutes. After addition was complete, the mixture was heated for a further 2 hours at 80° C. Subsequently, 7.8 g (30 mmol) of 1,6-bis(methyldichlorosilyl)hexane in 10 ml of toluene were added dropwise at from 0° to 5° C. over a period of 2 minutes and the mixture was stirred for a further 1 hour at room temperature. The solvents were removed and the residue was taken up in toluene and precipitated LiCl was subsequently filtered off. A suspension of isopropylcyclopentadienyllithium (prepared by reacting 6.5 g (60 mmol) of isopropylcyclopentadiene in 100 ml of toluene and 10 ml of diethyl ether at room temperature with 22 ml (60 mmol) of a 20% strength solution of butyllithium in toluene and stirring for a further 1 hour at room temperature) was added dropwise at room temperature to the filtrate over a period of 30 minutes and the mixture was subsequently stirred for a further 2 hours at room temperature. The reaction mixture was admixed with 100 ml of water, the phases were separated and the organic phase was washed with 50 ml of water. The solvents were removed in vacuo and the residue was purified by chromatography on 700 g of silica gel (hexane/methylene chloride 10:1). This gave 13.3 g (63%) of the ligand system of compound 6 as a very viscous oil. 30 ml (80 mmol) of a 20% strength solution of butyllithium in toluene were added dropwise at room temperature to a solution of 13 g (18 mmol) of the ligand system of compound 6 in 150 ml of diethyl ether over a period of 30 minutes. After addition was complete, the mixture was heated for a further 2 hours under reflux, the solvent was removed in vacuo and the residue was filtered using hexane through a G3 Schlenk frit. The tetralithium salt was dried for a number of hours in an oil pump vacuum at room temperature and subsequently added at −78° C. to a suspension of 8.15 g (35 mmol) of zirconium tetrachloride in 150 ml of methylene chloride. The cooling bath was removed and the mixture was stirred for a further 1 hour at room temperature. The reaction mixture was filtered through a G3 Schlenk frit, the residue was further extracted with a total of 300 ml of methylene chloride and the combined filtrates were evaporated in vacuo to about ⅓ of their volume. At −20° C., 4,6 g (27%) of compound 6 crystallized therefrom as a yellow amorphous solid.

$^1$H-NMR (100 MHz, CDCl$_3$): 7.1 to 8.2 (m, 16 H, arom. H), 5.5, 5.7, 6.3 (3m, 6H, H-Cp), 2.9 (m, 2H, i-propyl), 1.0 to 2.0 (m, 30 H, 4CH$_2$, CH$_2$Si, CH$_3$Si and CH$_3$-i-propyl).

G. 1,6-{Bis[methysilyldiindenyl)zirconiumdichloride]}hexane (7)

20 g (172 mmol) indene, 64.2 ml (172 mmol) butyllithium (20% in toluene) and 12.8 g (42 mmol) 1,6-bis (methyldichlorosilyl)hexane have been reacted as described in example A. Filtration over 250 g of silica (hexane/methylenechloride 5:1) gave 14.1 g (53%) of the ligand system as a viscous oil.

14.0 g (22 mmol) of the ligand system, 37.3 ml (100 mmol) butyllithium (20% in toluene) and 10.1 g (44 mmol) zirconiumtetrachloride have been reacted analogous to the procedure described in example A. Complex 3 precipitated at −30° C. from a toluene solution as a yellow amorphous powder. The yield was 9.0 g (43%)7.

$^1$H-NMR (100 MHz, CDCl$_3$): 6.8 to 7.6 (m, 20 H, arom. H und β-H-indene), 6.0 to 6.2 (m, 4H, α-H-indene); 1.2 to 2.0 (m, 12 H, 4 CH$_2$ und 2 CH$_2$Si); 0.9 bis 1.3 (3 s, broad, 6 H, Si—CH$_3$). Mass spectrum: 951 M$^+$, correct fragmentation pattern.

H. 1,6-{Bis[methylsilyl-bis(2-methyl-4,5-benzoindenyl)zirconiumdichloride]}-hexane (8)

1,6-{Bis[methylsilyl-bis(2-methyl-4,5-benzoindenyl)zirconiumdichloride]}hexane was synthesized in the manner as in example A. From the reaction of 57.8 g (320 mmol) 2-methyl-4,5-benzoindene, 119 ml (320 mmol) butyllithium (20% by weight in toluene) and 23.5 g (80 mmol) 1,6-Bis (methyldichlorosilyl)hexane was obtained 30.2 g (43%) of the ligand. The reaction of 29.6 g (33 mmol) ligand with 50 ml (134 mmol) butyllithium (20% by weight in toluene) and 13.3 g (57 mmol) of ZrCl$_4$ gave 12.4 g (35%) 8.

$^1$H-NMR (100 MHz, CDCl$_3$): 8.0–6.9 (m, 28 H, arom. H, b-H-indene); 2.3–2.2 (m, 12 H, Me-indene); 1,6–1.2 (m, 18 H, 6 CH$_2$ and 2 SiCH$_3$). Mass spectrum: 1207 M$^+$, correct fragmentation pattern.

I. 1,2-{Bis[methylsilyl-bis(2-methyl-4,5-benzoindenyl)zirconiumdichloride]}-ethane (9)

1,2-{Bis[methylsilyl-bis(2-methyl-4,5-benzoindenyl)zirconiumdichloride]}ethane was synthesized in the manner as in example B. From the reaction of 72.7 g (403 mmol) 2-methyl-4,5-benzoindene, 150 ml (403 mmol) butyllithium (20% by weight in toluene) and 23.5 g (92 mmol) 1,2-bis (methyldichlorosilyl)ethane was obtained 29.8 g (39%) of the ligand.

The reaction of 15.7 g (19 mmol) ligand with 30 ml (80 mmol) butyllithium (20% by weight in toluene) and 8.8 g (38 mmol) of ZrCl$_4$ gave 13.5 g (62%)9.

$^1$H-NMR (100 MHz, CDCl$_3$): 8.0–6.9 (m, 28 H, arom. H, b-H-indene); 2.3–2.2 (m, 12 H, Me-indene); 1.4–1.2 (m, 10 H, 2 CH$_2$ and 2 SiCH$_3$). Mass spectrum: 1151 M$^+$, correct fragmentation pattern.

POLYMERIZATION EXAMPLES

Example 1

A dry 16 dm$^3$ reactor was first flushed with nitrogen and then with propylene and charged with 10 dm$^3$ of liquid propylene. 30 cm$^3$ of methylaluminoxane solution in toluene were then added and the mixture was stirred at 30° C. In parallel thereto, 3.4 mg of the metallocene 1 were dissolved in 20 cm$^3$ of methylaluminoxane solution in toluene (23 mmol Al) and reacted by allowing to stand for 15 minutes. The solution was then added to the reactor, heated (4° C./min) to the polymerization temperature of 50° C. by supply of heat and the polymerization system was maintained at 50° C. for 1 hour by means of cooling. The polymerization was stopped by addition of 20 ml of isopropanol, the excess monomer was vented and the polymer was dried in vacuo. This gave 0.17 kg of polypropylene.

The catalyst activity was 50 kg PP/g metallocene ·h. VN=1041 cm$^3$/g; mp.=154° C.; the proportion extractable with heptane was 1.3%; M$_w$/M$_n$=6.4.

Example 2

The polymerization of Example 1 was repeated, except that 4.3 mg of the metallocene 1 were used and the polymerization temperature was 60° C. This gave 0.45 kg of polypropylene.

The catalyst activity was 105 kg PP/g metallocene ·h. VN=764 cm³/g; mp.=154° C.; the proportion extractable with heptane is 1.9%; $M_w/M_n$=2.9.

Example 3

The polymerization of Example 1 was repeated, except that 4.4 mg of the metallocene 1 were used and the polymerization temperature was 70° C. This gave 1.08 kg of polypropylene. The reactor has only very thin deposits on the interior wall and stirrer.

The catalyst activity was 245 kg PP/g metallocene ·h. VN=518 cm³g; mp.=153° C.; the proportion extractable with heptane is 2.4%; $M_w/M_n$=2.7.

Example 4

The polymerization of Example 1 was repeated, except that 2.7 mg of the metallocene 2 were used. This gave 0.17 kg of polypropylene.

The catalyst activity was 31 kg PP/g metallocene ·h. VN=845 cm³/g; mp.=154° C.; $M_w/M_n$=3.7; the proportion extractable with heptane is 7.7%.

Example 5

The polymerization of Example 1 was repeated, except that 4.3 mg of the metallocene 2 were used and the polymerization temperature was 60° C. This gave 0.71 kg of polypropylene.

The catalyst activity was 74 kg PP/g metallocene ·h. VN=564 cm³/g; mp.=153° C.; $M_w/M_n$=3.0; the proportion extractable with heptane is 4.6%.

Example 6

The polymerization of Example 1 was repeated, except that 3.8 mg of the metallocene 2 were used and the polymerization temperature was 70° C. This gave 0.95 kg of polypropylene. The reactor has only very thin deposits on the interior wall and stirrer.

The catalyst activity was 125 kg PP/g metallocene ·h. VN=392 cm³/g; mp.=153° C.; $M_w/M_n$=2.6; the proportion extractable with heptane is 4.1%.

Example 7

A dry 24 dm³ reactor was flushed with propylene and charged with 12 dm³ of liquid propylene. 30 cm³ of methylaluminoxane solution in toluene (40 mmol Al) were then added and the mixture was stirred at 30° C. for 5 minutes.

In parallel thereto, 2.0 mg of compound 3 were dissolved in 15 cm³ of methylaluminoxane solution in toluene (20 mmol Al) and reacted by allowing to stand for 5 minutes. The solution was then added to the reactor, heated (7° C./min) to the polymerization temperature of 70° C. by supply of heat and the polymerization system maintained at 70° C. for 1 hour by means of cooling. The polymerization was stopped by addition of 10 standard dm³ of $CO_2$ gas. The excess monomer was vented, the polymer was dried in vacuo. This gave 0.51 kg of polypropylene.

The catalyst activity was 255 kg PP/g metallocene×h. VN=365 cm³/g; mp.=154° C.;
II=97.5%; MFI (230/5)=2.8 dg/min;
$M_w$=517,599 g/mol, $M_w/M_n$=2.4.

Example 8

The procedure of Example 7 was repeated, but the polymerization temperature was 50° C. The catalyst activity was 134 kg PP/g metallocene×h.
VN=517 cm³/g; mp.=159° C.;
II=98.4%; MFI (230/5)=0.9 dg/min;
$M_w$=786,500 g/mol, $M_w/M_n$=2.4.

Example 9

The procedure of Example 7 was repeated, but the metallocene used was compound 4.

The catalyst activity was 402 kg PP/g metallocene×h. VN=142 cm³/g; mp.=152° C.;
II=96.9%; MFI (230/5)=86 dg/min;
$M_w$=153,500 g/mol, $M_w/M_n$=2.0.

Example 10

The procedure of Example 9 was repeated, but the polymerization temperature was 50° C. The catalyst activity was 176 kg PP/g metallocene×h.
VN=237 cm³/g; mp.=155° C.;
II=97.9%; MFI (230/5)=20 dg/min;
$M_w$=301,500 g/mol, $M_w/M_n$=2.7.

Example 11

The procedure of Example 7 was repeated, but the metallocene used was compound 4 and the polymerization temperature was 50° C.

The catalyst activity was 101 kg PP/g metallocene×h. VN=476 cm³/g; mp.=157° C.;
II=98%; MFI (230/5)=1.8 dg/min;
$M_w$=698,500 g/mol, $M_w/M_n$=5.8.

Example 12

A dry 24 dm³ reactor was flushed with propylene and charged with 12 standard dm³ of hydrogen and 12 dm³ of liquid propylene. 30 cm³ of methylaluminoxane solution in toluene (corresponding to 40 mmol Al) were then added.

Parallel thereto, 2.5 mg of compound 3 were dissolved in 15 cm³ of methylaluminoxane solution in toluene (20 mmol Al) and preactivated by allowing to stand for 5 minutes.

The solution was then added to the reactor and, with the addition of 60 g of ethylene, polymerization was carried out for 2 hours at 60° C. The metallocene activity was 205 kg PP/g metallocene×h. The ethylene content of the copolymer was 5.4% by weight.
VN=339 cm³/g, $M_w$=384,000 g/mol, $M_w/M_n$=2.0, mp.=136° C., according to NMR spectroscopy, the ethylene was predominantly incorporated in an isolated form (random copolymer).

Example 13

A dry 150 dm³ reactor was flushed with nitrogen and charged at 20° C. with 80 dm³ of a de-aromatized petroleum fraction having a boiling range from 100° to 120° C. The gas space was then flushed free of nitrogen by pressurizing 5 times with 2 bar of propylene and depressurizing.

After addition of 50 l of liquid propylene, 75 cm³ of methylaluminoxane solution in toluene (corresponding to 100 mmol Al) were added and the reactor contents were heated to 50° C. By metering in hydrogen, a hydrogen content of 2.0% was set in the gas space of the reactor and later kept constant during the entire propylene copolymerization time by metering in further amounts (on-line testing by gas chromatography). 16.0 mg of compound 3 were dissolved in 37.5 ml of methylaluminoxane solution in toluene (corresponding to 50 mmol Al) and added to the reactor after 15 minutes.

By means of cooling, the reactor was maintained at a polymerization temperature of 50° C. for 11 hours. After venting hydrogen and propylene to a propylene pressure in the reactor of 1.0 bar and after addition of 2.5 kg of ethylene, polymerization was continued for 5 hours at 50° C. The polymerization was then stopped by addition of 2 bar of $CO_2$ gas and the polymer formed was separated off from the suspension medium on a pressure filter. The product was dried for 24 hours at 80° C./200 mbar. This gave 17.5 kg of block copolymer powder, corresponding to a metallocene activity of 1093 kg PP/g metallocene×h.

VN=209 $cm^3$/g; $M_w$=217,500 g/mol; $M_w/M_n$=2.3; mp.=156° C.; MFI (230/5)=12 dg/min. The block copolymer contained 12.2% by weight of ethylene. Fractionation gave a content of 28.4% by weight of ethylene/propylene rubber. The glass transition temperature of the rubber was –52° C.

Example 14

Example 7 was repeated, but in addition 2.5 standard $dm^3$ of hydrogen were metered into the reactor prior to addition of the propylene.

The metallocene activity was 589 kg PP/g metallocene×h. VN=139 $cm^3$/g; $M_w$=149,500 g/mol, $M_w/M_n$=1.9; mp.=158° C.

Example 15

A dry 16 $dm^3$ reactor was flushed first with nitrogen and then with propylene and charged with 10 $dm^3$ of liquid propylene. 30 $cm^3$ of methylaluminoxane solution in toluene were then added and the mixture was stirred at 30° C. Parallel thereto, 3.0 mg of 5 were dissolved in 20 $cm^3$ of a methylaluminoxane solution in toluene (23 mmol Al) and reacted by allowing to stand for 15 minutes. The solution was then added to the reactor, heated (4° C./min) to the polymerization temperature of 50° C. by supply of heat and the polymerization system was maintained at 50° C. for 1 hour by means of cooling. The polymerization was stopped by addition of 20 ml of isopropanol, the excess monomer was vented and the polymer was dried in vacuo. This gave 0.56 kg of polypropylene. The reactor had essentially no deposits on the interior wall and stirrer.

The catalyst activity was 189 kg PP/g metallocene ·h; VN=449 $cm^3$/g; mp.=158° C.; $M_w$=529,500 g/mol; $M_w/M_n$= 2.2.

Example 16

The polymerization of Example 1 was repeated, except that 5.6 mg of compound 6 were used and the polymerization temperature was 70° C. This gave 0.17 kg of rubber-like polypropylene. The reactor had essentially no deposits on the interior wall and stirrer.

The catalyst activity was 30 kg PP/g metallocene ·h; VN=80 $cm^3$/g; isotactic pentads ($^{13}$C-NMR)=58%.

Examples 17–22

Example 12 was repeated with higher amounts of comonomers. The results are listed in table 1 (random copolymers; copolymer rubber)

Examples 23–32

A dry 1.5 $dm^3$ reactor was flushed with nitrogen and charged at 20° C. with 0.75 $dm^3$ of a benzine, from which the aromatic components had been removed (Exxsol DSP 100/120). The gas space of the reactor was then flushed free of nitrogen by injecting 2 bar of ethylen an decompressing the reactor (5 times). 2.6 $cm^3$ of a toluene solution of methylaluminoxane (3.5 mmol of Al, p=20) were then added. The reactor was heated up to 30° C. (15 minutes) and at a stirring rate of 500 rpm the desired monomer ratio of propylene and ethylene was established (partial pressures of propylene and ethylene see table 2). For the production of terpolymers 5-ethylidene-2-norbornene was additional added to the polymerization system (amounts see table 2). In parallel, 0.125 mg of metallocene 1 was dissolved in 1.25 $cm^3$ of a toluene solution of methylaluminoxane (1.67 mmol of Al, p=20) and left to stand for 5 minutes to achieve full reaction. The solution was then injected into the reactor. The polymerization system was then heated up to 50° C. and kept at this temperature for one hour. The reaction was terminated by addition of 2 ml of isopropanol.

Activities of the metallocene and product properties see table 2.

Examples 33–35

Example 3 was repeated, instead of metallocene 1 the metallocenes 7 (Ex. 33), 8 (Ex. 34) and 9 (Ex. 35) were used. For results of the polymerizations see table 3.

TABLE 1

| example | 12 | 17 | 18 | 19 | 20 | 21 | 22 |
|---|---|---|---|---|---|---|---|
| comonomer | 60 g ethylene | 150 g ethylene | 300 g ethylene | 500 g ethylene | 1 kg ethylene | 100 g 1-hexene | 100 g 4-methyl-1-pentene |
| met. activity [kg copolymer/g met × h] | 205 | 298 | 279 | 322 | 299 | 238 | 198 |
| comonomer cont. [wt.-%] i. copolymer | 5.4 | 8.9 | 19.8 | 30 | 62.4 | 3.8 | 4.6 |
| melting point [°C.] | 136 | 103 | — | — | — | 132 | 128 |
| glass transition temperature $T_g$ [°C.] | –10 | –22 | –38 | –48 | –50 | –12 | –11 |

TABLE 2

| example | 23 | 24 | 25 | 26 | 27 | 28 | 29 | 30 | 31 | 32 |
|---|---|---|---|---|---|---|---|---|---|---|
| partial pressure propylene [bar] | 2.5 | 2 | 1 | 1 | 1 | 2 | 1 | 1 | 1 | 1 |
| partial pressure ethylene [bar] | — | 2 | 3 | 4 | 5 | 3 | 3 | 3 | 3 | 3 |
| 5-ethylidene-2-norbornene [ml] | — | — | — | — | — | — | 1.25 | 2,5 | 5 | 10 |
| met. activity [kg polymer/g met × h] | 80 | 118 | 159 | 149 | 201 | 121 | 102 | 138 | 96 | 89 |
| viscosity number VN [cm³/g] | n.m. | 129 | 132 | 120 | 114 | 104 | 69 | 58 | 63 | 65 |
| ethylene cont. [wt.-%] in the polymer | — | 11.5 | 22 | 38 | 58 | 25 | 30 | 28 | 35 | 33 |
| ethylidene-norbornene cont. [wt.-%] in the polymer | — | — | — | — | — | — | 2.4 | 4.2 | 5.9 | 8.7 |
| glass transition temperature $T_g$ [°C.] | n.m. | −25.4 | −43.3 | −47.5 | −52.6 | −40.6 | −51 | −51.6 | −57.3 | −59.8 |

TABLE 3

| example | 33 | 34 | 35 |
|---|---|---|---|
| met. activity [kg PP/g met × h] | 296 | 219 | 196 |
| VN [cm³/g] | 54 | 294 | 269 |
| melting point [°C.] | 141 | 145 | 148 |
| $M_w/M_n$ | 2.3 | 2.5 | 2.1 |

Example 36

Use of a Supported Metallocene:

a) Preparation of the supported cocatalyst

The supported cocatalyst was prepared as described in EP 578 838 in the following way in an explosion-proofed stainless-steel reactor fitted with a 60 bar pump system, inert-gas supply, temperature control by jacket cooling and a second cooling circuit via a heat exchanger in the pump system. The pump system drew the contents out of the reactor via a connector in the reactor through a riser pipe via a heat exchanger. The mixer was installed in such a way that a narrowed tube cross-section, where an increased flow rate occurred, was formed in the feed line, and a thin feed line through which—in cycles—in each case a defined amount of water under 40 bar of argon could be fed in run into its turbulence zone axially and against the flow direction. The reaction was monitored via a sampler in the pump circuit.

5 dm³ of decane were introduced under inert conditions into the above-described reactor with a capacity of 16 dm³. 0.3 dm³ (=3.1 mol) of trimethylaluminum were added at 25° C. 250 g of silica gel SD 321 6-30 (Grace AG) which had previously been dried at 120° C. in an argon fluidized bed were then metered into the reactor via a solids funnel and homogeneously distributed with the aid of the stirrer and the pump system. The total amount of 45.9 g of water was added to the reactor in portions of 0.1 cm³ every 15 seconds over the course of 2 hours. The pressure, caused by the argon and the evolved gases, was kept constant at 10 bar by pressure-regulation valves. When all the water had been introduced, the pump system was switched off and the stirring was continued at 25° C. for a further 5 hours. The solvent was removed via a pressure filter, and the cocatalyst solid was washed with decane and then dried in vacuo. The isolated solid contains 18.7% by weight of aluminum. 15 g of this solid (104 mmol of Al) were suspended in 100 cm³ of this toluene in a stirrable vessel and cooled to −30° C. At the same tine, 200 mg of the metallocene 1 were dissolved in 75 cm³ of toluene and added dropwise to the suspension over the course of 30 minutes. The mixture was slowly warmed to room temperature with stirring, during which time the suspension took on a red color. The mixture was subsequently stirred at 70° C. for 1 hour, cooled to room temperature and filtered, and the solid was washed 3 times with 100 cm³ of toluene in each case and once with 100 cm³ of hexane. The hexane-moist filter residue whick remained was dried in vacuo, giving 12.7 mg of zirconocene per gram of catalyst.

b) Polymerization 1.0 g of the catalyst prepared under a) were suspended in 25 cm³ of a benzine fraction having the boiling range 100°–120° C. (Exxsol DSP 100/120). In paralell, a dry 24 dm³ reactor was flushed first with nitrogen and subsequently with propylene and filled with 12 dm³ of liquid propylene and with 1.5 dm³ of hydrogen. 3 cm³ triisobutylaluminium (12 mmol) were then diluted with 30 ml of hexane and introduced into the reactor, and the batch was stirred at 30° C. for 15 minutes. The catalyst suspension was subsequently introduced into the reactor, and the polymerization system was heated to the polymreization temperature of 70° C. (10° C./min), and kept at 70° C. for 1 hour by cooling. The polymerization was terminated by addition of 20 ml of isopropanol. The excess monomer was removed as a gas, and the poylmer was dried in vacuo, giving 2.4 kg of polypropylene powder.

Fractionation of the polymer by heptane extraction gave an heptane soluble content of 0.9% by weight (VN=112 cm³/g) and an insoluble content of 99.1% by weight (VN= 469 cm³/g). The granules prepared in this contained no fines <250 μm, the $d_{50}$ value was 980 μm (average particle size).

Example 37

0.125 mg of metallocene 1 was solved in 1.25 ml MAO/toluene solution and mixed for 15 minutes. Meanwhile a stirred inert 1.5 dm³ reactor is filled with 750 ml inert diesel oil (b.p. 100°–120° C.) and 3.75 ml MAO/toluene solution. The reactor is heated up to 70° C. and the polymerization started by adding the catalyst solution at 750 rpm with 5 bar ethylene. After 1 hour the reactor is decompressed, and the polymer filtered off from the suspension, washed with acetone and dried for 12 h in a vacuum drying cabinet. 31 g polyethylen powder was recovered, corresponding to 248 kgPE/g metallocene/h, with VN=520 cm³/g. The polydispersity is $M_w/M_n=2.7$.

Example 38

Example 37 was repeated with 0.125 mg of metallocene 2.40.8 g PE was recovered, corresponding to 326 kgPE/g metallocene/h, with VN=720 cm³/g. $M_w/M_n=2.8$.

Example 39

Example 37 was repeated with 0.5 bar hydrogen applied before addition of ethylen. 35 g PE was recovered, with VN=75 cm³/g. $M_w/M_n=2.8$.

Example 40

Example 39 was repeated with 1 bar hydrogen insted of 0.5 bar. 28 g PE wax was recovered, with VN=22 cm³/g. The melt viscosity at 140° C. was 550 mPas. $M_w/M_n=2.6$

Example 41

Example 37 was repeated with 0.4 mg of metallocene 7.25.1 g PE was recovered, corresponding to 62 kgPE/g metallocene/h, with VN=340 cm³/g. $M_w/M_n=2.8$.

Example 42

Example 37 was repeated with 0.125 mg of metallocene 8.24 g PE was recovered, corresponding to 192 kgPE/g metallocene/h, with VN=440 cm³/g. $M_w/M_n=2.8$.

Example 43

Example 37 was repeated with 0.125 mg of metallocene 9.30 g PE was recovered, corresponding to 240 kgPE/g metallocene/h, with VN=495 cm³/g. $M_w/M_n=2.7$.

Example 44

Example 43 was repeated with additional 20 ml 1-hexene added together with the diesel oil. The polymerization was stopped after 15 minutes by addition of 0.5 bar $CO_2$. 9 g ethylene/1-hexene copolymer was recovered, corresponding to 288 kgPE/g metallocene/h, with VN=250 cm³/g. 8.96 mol % hexene was found in copolymer by $^{13}C$-NMR.

We claim:

1. A process for preparing an olefin polymer by polymerization of at least one olefin in the presence of a catalyst which contains at least one polynuclear metallocene and at least one cocatalyst, wherein the polynuclear metallocene is a compound of the formula I

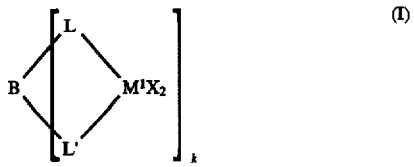

where $M^1$ are identical or different and are a metal of group IVb, Vb or VIb of the Periodic Table, X are identical or different and are hydrogen, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-aryl-alkenyl group, an OH group, a halogen atom or pseudohalogen, L and L' are identical or different and are a π ligand or another electron donor, k is 2 if $B^1$ is

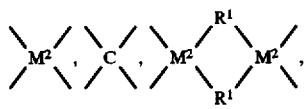

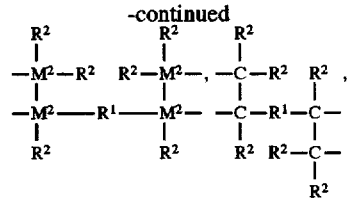

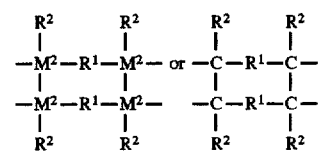

and k is an integer >1 if $B^1$ is

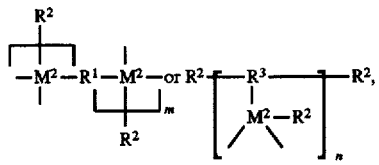

where the radicals $R^1$ are identical or different and are a divalent hydrocarbon-containing bridge structure, the radicals $R^2$ are identical or different and are a hydrogen atom, a halogen atom or a hydrocarbon-containing radical, $R^3$ is a trivalent hydrocarbon-containing radical, and n is k and m is k–1 and $M^2$ is silicon, germanium or tin.

2. The process as claimed in claim 1, wherein said cocatalyst is an aluminum compound.

3. The process as claimed in claim 2, wherein said aluminum compound is an aluminoxane and/or an aluminum alkyl.

4. The process as claimed in claim 3, wherein said aluminoxane is of the formula IIIa for the linear type and/or of the formula IIIb for the cyclic type,

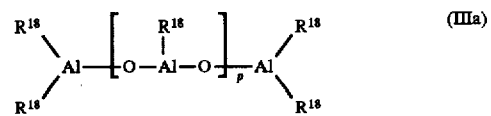

wherein in the formulae IIIa and IIIb, the radicals $R^{18}$ can be identical or different and are a $C_1$–$C_6$-alkyl group, a $C_6$–$C_{18}$-aryl group, benzyl or hydrogen, and p is an integer from 2 to 50.

5. The process as claimed in claim 4, wherein $R^{18}$ are identical and are methyl, isobutyl, phenyl or benzyl.

6. The process as claimed in claim 4, wherein p is an integer from 10 to 35 and the radicals $R^{18}$ are different.

7. The process as claimed in claim 6, wherein the radicals $R^{18}$ are different and are methyl and hydrogen or methyl, isobutyl and hydrogen.

8. The process as claimed in claim 7, wherein isobutyl is present in an amount from 0.1 to 40% based on the total of amount $R^{18}$.

9. The process as claimed in claim 4, wherein the aluminoxane is in a solution in the range from about 1% by weight to the saturation limit based on the total amount of solution.

10. The process as claimed in claim 9, wherein the aluminoxane is in a solution in an amount from 5 to 30% by weight based on the total amount of solution.

11. The process as claimed in claim 1, wherein the compound of formula I is selected from the group consisting of 1-indenyl, 2-alkyl-4-aryl-1-indenyl, 2,4-dialkyl-1-indenyl, 2,4-dialkyl-1-indenyl, 2,4,6-trialkyl-1-indenyl, 1-alkyl-α-acenaphth-1-indenyl, 1-alkyl-4,5-benzo-1-indenyl, 2,5-dialkyl-1-indenyl, 2,5,6-trialkyl-1-indenyl, 2,4,5-trialkyl-1-indenyl, 2-alkyl-1-indenyl, 2-aryl-1-indenyl, 2,6-dialkyl-4-aryl-1-indenyl, 2-alkyl-5-aryl-1-indenyl, 2-alkyl-5,6-dialkyl-1-indenyl, 2-alkyl-4,5-dialkyl-1-indenyl, 2-aryl-4,6-dialyl-1-indenyl, fluorenyl, 2,7-dialkylfluorenyl, or 4-alkylfluorenyl, 2-alkyl-1-cyclopentadienyl, 2,4-dialkyl-1-cyclopentadienyl, 2,4,5-trialkyl-1-cyclopentadienyl, 2-Si(trialkyl)-1-cyclopentadienyl, 2-Si(trialkyl)-4-alkyl-1-cyclopentadienyl, 2-Si(trialkyl)-4,5-dialkyl-1-cyclopentadienyl, 2-alkyl-4-aryl-1-cyclopentadienyl, 2,5-alkyl-4-aryl-1-cyclopentadienyl, 2,4-alkyl-5-aryl-1-cyclopentadienyl, 2-aryl-1-cyclopentadienyl, 2-aryl-4-alkyl-1-cyclopentadienyl, 2-aryl-4,5 alkyl-1-cyclopentadienyl or 2-aryl-4,5-aryl-1-cyclopentadienyl, 1,6-bis[methylsilyl(fluorenyl)(cyclopentadienyl)zirconium dichloride]hexane, 1,6-bis[methylsilyl(indenyl)(cyclopentadienyl)zirconium dichloride]hexane, 1,6-bis[methylsilyl(fluorenyl)(3-methylcyclopentadienyl) zirconium dichloride]hexane, 1,6-bis[methylsilyl(indenyl)(3-methylcyclopentadienyl) zirconium dichloride]hexane, 1,6-bis[methylsilyl-(fluorenyl(3-isopropylcyclopentadienyl)zirconium dichloride]hexane, 1,6-bis[methylsilyl-(indenyl)(3-isopropylcyclopentadienyl) zirconium dichloride]hexane, 1,6-bis[methylsilyl-(2,7-di-tert-butylfluorenyl) (cyclopentadienyl)zirconium dichloride]hexane, 1,6-bis[methylsilyl-(2-methylindenyl)(cyclopentadienyl) zirconium dichloride]hexane, 1,4-disilacyclohexane-1,4-diylidene[(2-methyl-4-phenylindenyl)(2-methyl-4,6-diisopropylindenyl) zirconium dichloride], 1,4-disilacyclohexane-1,4-diylidene[(2-methyl-4-phenylindenyl(2-methyl-4,5-benzoindenyl)zirconium dichloride], 1,4-disilacyclohexane-1,4-diylidene[(2-methyl-4-phenylindenyl(2-ethyl-4-phenylindenyl)zirconium dichloride], 1,4-disilacyclohexane-1,4-diylidene[(2-methyl-4-phenylindenyl)(2-methyl-α-methylacenaphthindenyl) zirconium dichloride], 9,10-dihydro-9,10-disilaanthracene-9,10-diylidene[(2-methyl-4-phenylindenyl)(indenyl)zirconium dichloride], 9,10-dihydro-9,10-disilaanthracene-9,10-diylidene[(2-methyl-4-phenylindenyl)(2-methylindenyl)zirconium dichloride], 9,10-dihydro-9,10-disilaanthracene-9,10-diylidene[(2-methyl-4-phenylindenyl)(2-ethylindenyl)zirconium dichloride], 9,10-dihydro-9,10-disilaanthracene-9,10-diylidene[(2-methyl-4-phenylindenyl(2-methyl-4-isopropylindenyl) zirconium dichloride), 9,10-dihydro-9,10-disilaanthracene-9,10-diylidene[(2-methyl-4-phenylindenyl)(2- methyl-4,6-diisopropylindenylzirconium dichloride], 9,10-dihydro-9,10-disilaanthracene-9,10-diylidene[(2-methyl-4-phenylindenyl)(2-methyl-4,5-benzoindenyl) zirconium dichloride), 9,10-dihydro-9,10-disilaanthracene-9,10-diylidene[(2-methyl-4-phenylindenyl)(2-ethyl-4-phenylindenyl) zirconium dichloride, 9,10-dihydro-9,10-disilaanthracene-9,10-diylidene[(2-methyl-4-phenylindenyl)(2-methyl-α-acenaphthindenyl) zirconium dichloride), 1,4-dihydro-1,4-disilabenzene-1,4-diylidene[(2-methyl-4-phenylindenyl)(indenyl)zirconium dichloride], 1,4-dihydro-1,4-disilabenzene-1,4-diylidene[(2-methyl-4-phenylindenyl)(2-methylindenyl)zirconium dichloride], 1,4-dihydro-1,4-disilabenzene-1,4-diylidene[(2-methyl-4-phenylindenyl)(2-ethylindenyl)zirconium dichloride], 1,6-bis[methylsilyl-(2-methyl-4-phenylindenyl (cyclopentadienyl)zirconium dichloride]hexane, 1,6-bis[methylsilyl-(4-phenylindenyl)(cyclopentadienyl)-zirconium dichloride]hexane, 1,6-bis[methylsilyl-(2-methyl-4-phenylindenyl)(2,3,5-trimethylcyclopentadienyl)zirconium dichloride]hexane, 1,6-bis[methylsilyl-(fluorenyl)(3-phenylcyclopentadienyl) zirconium dichloride]hexane, 1,6-bis[methylsilyl-(indenyl)(3-phenylcyclopentadienyl)-zirconium dichloride]hexane, 1,6-bis[methylsilyl-(2-methyl-4,5-benzoindenyl) (cyclopentadieny)zirconium dichloride]hexane, 1,6-bis[methylsilyl-(2-methyl-4,6-diisopropylindenyl) (cyclopentadienyl)zirconium dichloride]hexane, 1,6-bis[methylsilyl-(2-methyl-4-(1-naphthylindenyl)- (cyclopentadienyl)zirconium dichloride]hexane, 1,6-bis[methylsilyl-(2-ethyl-4-phenylindenyl) (cyclopentadienyl)zirconium dichloride]hexane, 1,6-bis[methylsilyl-(2-methyl-4,5-benzoindenyl)(2,3,5-trimethylcyclopentadienyl)zirconium dichloride]hexane, 1,6-bis[methylsilyl-(2-methyl-4,6-diisopropylindenyl)(2,3,5-trimethylcyclopentadienyl)zirconium dichloride] hexane, 1,6-bis[methylsilyl-(2-methyl-4-(1-naphthylindenyl-(2,3,5-trimethylcyclopentadienyl)zirconium dichloride]hexane, 1,6-bis[methylsilyl-(2-ethyl-4-phenylindenyl)(2,3,5-trimethylcyclopentadienyl)zirconium dichloride]hexane, 1,2-bis[methylsilyl-(fluorenyl)(cyclopentadienyl)-zirconium dichloride]ethane, 1,2-bis[methylsilyl-(indenyl)(cyclopentadienyl)zirconium dichloride]ethane, 1,2-bis[methylsilyl-(fluorenyl)(3-methylcyclopenta-dienyl) zirconium dichloride]ethane, 1,2-bis[methylsilyl-(indenyl)(3-methylcyclopentadienyl)-zirconium dichloride]ethane, 1,2-bis[methylsilyl-(fluorenyl)(3-isopropylcyclopentadienyl)zirconium dichloride]ethane, 1,2-bis[methylsilyl-(indenyl)(3-isopropylcyclopentadienyl) zirconium dichloride]ethane, 1,2-bis[methylsilyl-(2,7-di-tert-butylfluorenyl) (cyclopentadienyl)zirconium dichloride]ethane, 1,2-bis[methylsilyl-(2-methylindenyl)(cyclopentadienyl)-zirconium dichloride]ethane, 1,2-bis[methylsilyl-(2-methyl-4-phenylindenyl) (cyclopentadienyl)zirconium dichloride]ethane, 1,2-bis[methylsilyl-(4-phenylindenyl)(cyclopentadienyl)-zirconium dichloride]ethane, 1,2-bis[methylsilyl-(2-methyl-4-phenylindenyl)(2,3,5-trimethylcyclopentadienyl)zirconium dichloride]ethane, 1,2-bis[methylsilyl-(fluorenyl)(3-phenylcyclopentadienyl) zirconium dichloride]ethane, 1,2-bis[methylsilyl-(indenyl)(3-phenylcyclopentadienyl)-zirconium dichloride]ethane, 1,2-bis[methylsilyl-(2-methyl-4,5-benzoindenyl)(cyclopentadienyl)zirconium dichloride]ethane,
1,2-bis[methylsilyl-(2-methyl-4,6-diisopropylindenyl)-(cyclopentadienyl)zirconium dichloride]ethane,
1,2-bis[methylsilyl-(2-methyl-4-(1-naphthylindenyl)-(cyclopentadienyl)zirconium dichloride]ethane,
1,2-bis[methylsilyl-(2-ethyl-4-phenylindenyl)(cyclopentadienyl)zirconium dichloride]ethane,
1,2-bis(methylsilyl-(2-methyl-4,5-benzoindenyl)(2,3,5-trimethylcyclopentadienyl)zirconium dichloride]ethane,
1,2-bis[methylsilyl-(2-methyl-4,6-diisopropylindenyl)(2,3,5-trimethylcyclopentadienyl)zirconium dichloride]ethane,
1,2-bis[methylsilyl-(2-methyl-4-(1-naphthylindenyl)(2,3,5-trimethylcyclopentadienyl)zirconium dichloride]-ethane,
1,2-bis[methylsilyl-(2-ethyl-4-phenylindenyl)(2,3,5-trimethylcyclopentadienyl)zirconium dichloride]ethane,
1,4-disilacyclohexane-1,4-diylidene[(fluorenyl)(cyclopentadienyl)zirconium dichloride],
1,4-disilacyclohexane-1,4-diylidene[(indenyl)(cyclopentadienyl)zirconium dichloride],
1,4-disilacyclohexane-1,4-diylidene[(fluorenyl)(3-methylcyclopentadienyl)zirconium dichloride],
1,4-disilacyclohexane-1,4-diylidene[(indenyl)(3-methylcyclopentadienyl)zirconium dichloride],
1,4-disilacyclohexane-1,4-diylidene[(fluorenyl)(3-isopropylcyclopentadienyl)zirconium dichloride],
1,4-disilacyclohexane-1,4-diylidene[(indenyl)(3-isopropylcyclopentadienyl)zirconium dichloride],
1,4-disilacyclohexane-1,4-diylidene[(2,7-di-tert-butyl-fluorenyl)(cyclopentadienyl)zirconium dichloride],
1,4-disilacyclohexane-1,4-diylidene[(2-methylindenyl)-(cyclopentadienyl)zirconium dichloride],
1,4-disilacyclohexane-1,4-diylidene[(2-methyl-4-phenyl-indenyl)(cyclopentadienyl)zirconium dichloride],
1,4-disilacyclohexane-1,4-diylidene[(4-phenylindenyl)-(cyclopentadienyl)zirconium dichloride],
1,4-disilacyclohexane-1,4-diylidene[(2-methyl-4-1phenyl-indenyl)(2,3,5-trimethylcyclopentadienyl)zirconium dichloride],
1,4-disilacyclohexane-1,4-diylidene[(fluorenyl)(3-phenylcyclopentadienyl)zirconium dichloride],
1,4-disilacyclohexane-1,4-diylidene[(indenyl)(3-phenylcyclopentadienyl)zirconium dichloride],
1,4-disilacyclohexane-1,4-diylidene[(2-methyl-4,5-benzo-indenyl)(cyclopentadienyl)zirconium dichloride],
1,4-disilacyclohexane-1,4-diylidene[(2-methyl-4,6-diisopropylindenyl)(cyclopentadienyl)zirconium dichloride],
1,4-disilacyclohexane-1,4-diylidene[(2-methyl-4-(1-napthylindenyl)(cyclopentadienyl)zirconium dichloride),
1,4-disilacyclohexane-1,4-diylidene[(2-ethyl-4-phenylindenyl)(cyclopentadienyl)zirconium dichloride],
1,4-disilacyclohexane-1,4-diylidene(2-methyl-4,5-benzo-indenyl)(2,3,5-trimethylcyclopentadienyl)zirconium dichloride],
1,4-disilacyclohexane-1,4-diylidene[(2-methyl-4,6-diisopropylindenyl)(2,3,5-trimethylcyclopentadienyl)zirconium dichloride],
1,4-disilacyclohexane-1,4-diylidene[(2-methyl-4-(1-naphthylindenyl)(2,3,5-trimethylcyclopentadienyl)-zirconium dichloride],
1,4-disilacyclohexane-1,4-diylidene[(2-ethyl-4-phenyl-indenyl)(2,3,5-trimethylcyclopentadienyl)zirconium dichloride],
9,10-dihydro-9,10-disilaanthracene-9,10-diylidene-[(fluorenyl)(cyclopemadieny)zirconium dichloride],
9,10-dihydro-9,10-disilaanthracene-9,10-diylidene-[(indenyl)(cyclopentadienyl)zirconium dichloride],
9,10-dihydro-9,10-disilaanthracene-9,10-diylidene-[(fluorenyl)(3-methylcyclopentadienyl)zirconium dichloride],
9,10-dihydro-9,10-disilaanthracene-9,10-diylidene[(indenyl)(3-methylcyclopentadienyl)zirconium dichloride],
9,10-dihydro-9,10-disilaanthracene-9,10-diylidene-[(fluorenyl)(3-isopropylcyclopentadienyl)zirconium dichloride],
9,10-dihydro-9,10-disilaanthracene-9,10-diylidene-[(indenyl)(3-isopropylcyclopentadienyl)zirconium dichloride],
9,10-dihydro-9,10-disilaanthracene-9,10-diylidene[(2,7-di-tert-butylfluorenyl)(cyclopentadienyl)zirconium dichloride],
9,10-dihydro-9,10-disilaanthracene-9,10-diylidene[(2-methylindenyl)(cyclopentadienyl)zirconium dichloride],
9,10-dihydro-9,10-disilaanthracene-9,10-diylidene[(2-methyl-4-phenylindenyl)(cyclopentadienyl)zirconium dichloride],
9,10-dihydro-9,10-disilaanthracene-9,10-diylidene[(4-phenylindenyl)(cyclopentadienyl)zirconium dichloride],
9,10-dihydro-9,10-disilaanthracene-9,10-diylidene[(2-methyl-4-phenylindenyl)(2,3,5-trimethylcyclopentadienyl)-zirconium dichloride],
9,10-dihydro-9,10-disilaanthracene-9,10-diylidene[(fluorenyl)(3-phenylcyclopentadienyl)zirconium dichloride],
9,10-dihydro-9,10-disilaanthracene-9,10-diylidene[(indenyl)(3-phenylcyclopentadieny)zirconium dichloride],
9,10-dihydro-9,10-disilaanthracene-9,10-diylidene[(2-methyl-4,5-benzoindenyl)(cyclopentadienyl)zirconium dichloride],
9,10-dihydro-9,10-disilaanthracene-9,10-diylidene[(2-methyl-4,6-diisopropylindenyl)(cyclopentadienyl)-zirconium dichloride],
9,10-dihydro-9,10-disilaanthracene-9,10-diylidene[(2-methyl-4-(1-naphthylindenyl)(cyclopentadienyl)zirconium dichloride],
9,10-dihydro-9,10-disilaanthracene-9,10-diylidene[(2-ethyl-4-phenylindenyl)cyclopentadienyl)zirconium dichloride],
9,10-dihydro-9,10-disilaanthracene-9,10-diylidene [(2-methyl-4,5-benzoindenyl)(2,3,5-trimethylcyclopentadieny)zirconium dichloride],
9,10-dihydro-9,10-disilaanthracene-9,10-diylidene[(2-methyl-4,6-diisopropylindenyl)(2,3,5-trimethylcyclopentadienyl)zirconium dichloride],
9,10-dihydro-9,10-disilaanthracene-9,10-diylidene[(2-methyl-4-(1-naphthylindenyl(2,3,5-trimethylcyclopentadienyl)zirconium dichloride],
9,10-dihydro-9,10-disilaanthracene-9,10-diylidene[(2-ethyl-4-phenylindenyl)(2,3,5-trimethylcyclopentadienyl)-zirconium dichloride],
1,6-bis[methylsilyl-bis(indenyl)zirconium dichloride] hexane,
1,6-bis[methylsilyl-bis(2-methylindenyl)zirconium dichloride]hexane,
1,6-bis[methylsilyl-bis(2-methyl-4-phenylindenyl)zirconium dichloride]hexane,
1,6-bis[methylsilyl-bis(2-methyl-4,5-benzoindenyl)zirconium dichloride]hexane,
1,6-bis[methylsilyl-bis(2-methyl-4-(1-naphthyl)indenyl)zirconium dichloride]hexane, 1,6-bis[methylsilyl-bis(2-methyl-4-isopropylindenyl)-
zirconium dichloride]hexane,
1,6-bis[methylsilyl-bis(2-methyl-4,6-diisopropylindenyl)-
zirconium dichloride]hexane,
1,6-bis[methylsilyl-bis(2-ethylindenyl)zirconium
dichloride]hexane,
1,6-bis[methylsilyl-bis(2-ethyl-4-phenylindenyl)-zirconium
dichloride]hexane,
1,6-bis[methylsilyl-bis(2-ethyl-4-(1-naphthyl)indenyl)-
zirconium dichloride]hexane,
1,6-bis[methylsilyl-bis(2-ethyl-α-acenaphthindenyl)-
zirconium dichloride]hexane,
1,2-bis[methylsilyl-bis(indenyl)zirconium dichloride]
ethane,
1,2-bis[methylsilyl-bis(2-methylindenyl)zirconium
dichloride]ethane,
1,2-bis[methylsilyl-bis(2-methyl-4-phenylindenyl)
zirconium dichloride]ethane,
1,2-bis[methylsilyl-bis(2-methyl-4,5-benzoindenyl)-
zirconium dichloride]ethane,
1,2-bis[methylsilyl-bis(2-methyl-4-(1-naphthyl)indenyl)-
zirconium dichloride]ethane,
1,2-bis[methylsilyl-bis2-methyl-4-isopropylindenyl)-
zirconium dichloride]ethane,
1,2-bis[methylsilyl-bis(2-methyl-4,6-diisopropylindenyl)-
zirconium dichloride]ethane,
1,2-bis[methylsilyl-bis(2-ethylindenyl)zirconium
dichloride]ethane,
1,2-bis[methylsilyl-bis(2-ethyl-4-phenylindenyl)-zirconium
dichloride]ethane,
1,2-bis[methylsilyl-bis(2-ethyl-4-(1-naphthyl)indenyl)-
zirconium dichloride]ethane,
1,2-bis[methylsilyl-bis(2-ethyl-α-acenaphthindenyl)-
zirconium dichloride]ethane,
1,2-bis[ethylsilyl-bis(indenyl)zirconium dichloride]ethane,
1,2-bis(ethylsilyl-bis(2-methylindenyl)zirconium
dichloride]ethane,
1,2-bis(ethylsilyl-bis(2-methyl-4-phenylindenyl)-zirconium
dichloride]ethane,
1,2-bis[ethylsilyl-bis(2-methyl-4,5-benzoindenyl)-
zirconium dichloride]ethane,
1,2-bis[ethylsilyl-bis(2-methyl-4-(1-naphthyl)indenyl)-
zirconium dichloride]ethane,
1,2-bis[ethylsilyl-bis(2-methyl-4-isopropylindenyl)-
zirconium dichloride]ethane,
1,2-bis[ethylsilyl-bis(2-methyl-4,6-diisopropylindenyl)-
zirconium dichloride]ethane,
1,2-bis[ethylsilyl-bis(2-ethylindenyl)zirconium dichloride]
ethane,
1,2-bis[ethylsilyl-bis(2-ethyl-4-phenylindenyl)zirconium
dichloride]ethane,
1,2-bis[ethylsilyl-bis(2-ethyl-4-(1-naphthyl)indenyl)-
zirconium dichloride]ethane,
1,2-bis[ethylsilyl-bis(2-ethyl-α-acenaphthindenyl)-
zirconium dichloride]ethane,
1,6-bis[ethylsilyl-bis(indenyl)zirconium dichloride]hexane,
1,6-bis[ethylsilyl-bis(2-methylindenyl)zirconium
dichloride]hexane,
1,6-bis[ethylsilyl-bis(2-methyl-4-phenylindenyl)zirconium
dichloride]hexane,
1,6-bis[ethylsilyl-bis(2-methyl-4,5-benzoindenyl)zirconium
dichloride]hexane,
1,6-bis[ethylsilyl-bis(2-methyl-4-(1-naphthyl)indenyl)-
zirconium dichloride]hexane,
1,6-bis[ethylsilyl-bis(2-methyl-4-isopropylindenyl)
zirconium dichloride]hexane,
1,6-bis[ethylsilyl-bis(2-methyl-4,6-diisopropylindenyl)
zirconium dichloride]hexane,
1,6-bis[ethylsilyl-bis(2-ethylindenyl)zirconium dichloride]
hexane,
1,6-bis[ethylsilyl-bis(2-ethyl-4-phenylindenyl)zirconium
dichloride]hexane,
1,6-bis[ethylsilyl-bis(2-ethyl-4-(1-naphthylindenyl)
zirconium dichloride]hexane,
1,6-bis[ethylsilyl-bis(2-ethyl-α-acenaphthindenyl)
zirconium dichloride]hexane,
1,3-bis[methylsilyl-bis(indenyl)zirconium dichloride]-
propane,
1,3-bis[methylsilyl-bis(2-methylindenyl)zirconium
dichloride]propane,
1,3-bis[methylsilyl-bis(2-methyl-4-phenylindenyl)
zirconium dichloride]propane,
1,3-bis[methylsilyl-bis(2-methyl-4,5-benzoindenyl)
zirconium dichloride]propane,
1,3-bis[methylsilyl-bis(2-methyl-4-(1-naphthyl)indenyl)-
zirconium dichloride]propane,
1,3-bis[methylsilyl-bis(2-methyl-4-isopropylindenyl)
zirconium dichloride]propane,
1,3-bis[methylsilyl-bis(2-methyl-4,6-diisopropylindenyl)-
zirconium dichloride]propane,
1,3-bis[methylsilyl-bis(2-ethylindenyl)zirconium
dichloride]propane,
1,3-bis[methylsilyl-bis(2-ethyl-4-phenylindenyl)zirconium
dichloride]propane,
1,3-bis[methylsilyl-bis(2-ethyl-4-(1-naphthyl)indenyl)
zirconium dichloride]propane,
1,3-bis[methylsilyl-bis(2-ethyl-α-acenaphthindenyl)
zirconium dichloride]propane,
1,4-disilacyclohexane-1,4-diylidene[bis(indenyl)zirconium
dichloride],
1,4-disilacyclohexane-1,4-diylidene[bis(2-methylindenyl)
zirconium dichloride],
1,4-disilacyclohexane-1,4-diylidene[bis(2-ethylindenyl)
zirconium dichloride],
1,4-disilacyclohexane-1,4-diylidene[bis(2-methyl-4-
phenylindenyl)zirconium dichloride],
1,4-disilacyclohexane-1,4-diylidene[bis(2-methyl-4-(1-
naphthylindenyl)zirconium dichloride],
1,4-disilacyclohexane-1,4-diylidene[bis(2-methyl-4-
isopropylindenyl)zirconium dichloride],
1,4-disilacyclohexane-1,4-diylidene[bis(2-methyl-4,6-
diisopropylindenyl)zirconium dichloride],
1,4-disilacyclohexane-1,4-diylidene[bis(2-methyl-4,5-
benzoindenyl)zirconium dichloride],
1,4-disilacyclohexane-1,4-diylidene[bis(2-ethyl-4-phenyl-
indenyl)zirconium dichloride],
1,4-disilacyclohexane-1,4-diylidene[bis(2-methyl-α-
acenaphthindenyl)zirconium dichloride],
9,10-dihydro-9,10-disilaanthracene-9,10-diylidene[bis
(indenyl)zirconium dichloride],
9,10-dihydro-9,10-disilaanthracene-9,10-diylidene[bis(2-
methylindenyl)zirconium dichloride],
9,10-dihydro-9,10-disilaanthracene-9,10-diylidene[bis(2-
ethylindenyl)zirconium dichloride],
9,10-dihydro-9,10-disilaanthracene-9,10-diylidene[bis(2-
methyl-4-phenylindenyl)zirconium dichloride],
9,10-dihydro-9,10-disilaanthracene-9,10-diylidene[bis(2-
methyl-4-(1-naphthylindenyl)zirconium dichloride],
9,10-dihydro-9,10-disilaanthracene-9,10-diylidene[bis(2-
methyl-4-isopropylindenyl)zirconium dichloride],
9,10-dihydro-9,10-disilaanthracene-9,10-diylidene[bis(2-
methyl-4,6-diisopropylindenyl)zirconium dichloride],
9,10-dihydro-9,10-disilaanthracene-9,10-diylidene[bis(2-
methyl-4,5-benzoindenyl)zirconium dichloride],
9,10-dihydro-9,10-disilaanthracene-9,10,-diylidene[bis(2-
ethyl-4-phenylindenyl)zirconium dichloride], 9,10- dihydro-9,10-disilaanthracene-9,10-diylidene[bis(2-methyl-α-acenaphthindenyl)zirconium dichloride], 1,4-dihydro-1,4-disilabenzene-1,4-diylidene[bis(indenyl)zirconium dichloride], 1,4-dihydro-1,4-disilabenzene-1,4-diylidene[bis(2-methylindenyl)zirconium dichloride], 1,4-dihydro-1,4-disilabenzene-1,4-diylidene[bis(2-ethylindenyl)zirconium dichloride], 1,4-dihydro-1,4-disilabenzene-1,4-diylidene[bis(2-methyl-4-phenylindenyl)zirconium dichloride], 1,4-dihydro-1,4-disilabenzene-1,4-diylidene[bis(2-methyl-4-(1-naphthylindenyl)zirconium dichloride], 1,4-dihydro-1,4-disilabenzene-1,4-diylidene[bis(2-methyl-4-isopropylindenyl)zirconium dichloride], 1,4-dihydro-1,4-disilabenzene-1,4-diylidene[bis(2-methyl-4,6-diisopropylindenyl)zirconium dichloride], 1,4-dihydro-1,4-disilabenzene-1,4-diylidene[bis(2-methyl-4,5-benzoindenyl)zirconium dichloride], 1,4-dihydro-1,4-disilabenzene-1,4-diylidene[bis(2-ethyl-4-phenylindenyl)zirconium dichloride], 1,4-dihydro-1,4-disilabenzene-4-diylidene[bis(2-methyl-α-acenaphthindenyl)zirconium dichloride], 1,4-dihydro-1,4-disila-2,3,5,6-tetraphenylbenzene-1,4-diylidene[bis(indenyl)zirconium dichloride], 1,4-dihydro-1,4-disila-2,3,5,6-tetraphenylbenzene-1,4-diylidene[bis(2-methylindenyl)zirconium dichloride], 1,4-dihydro-1,4-disila-2,3,5,6-tetraphenylbenzene-1,4-diylidene[bis(2-ethylindenyl)zirconium dichloride], 1,4-dihydro-1,4-disila-2,3,5,6-tetraphenylbenzene-1,4-diylidene[bis(2-methyl-4-phenylindenyl)zirconium dichloride], 1,4-dihydro-1,4-disila-2,3,5,6-tetraphenylbenzene-1,4-diylidene[bis(2-methyl-4-(1-naphthylindeny)zirconium dichloride], 1,4-dihydro-1,4-disila-2,3,5,6-tetraphenylbenzene-1,4-diylidene[bis(2-methyl-4-isopropylindenyl)zirconium dichloride, 1,4-dihydro-1,4-disila-2,3,5,6-tetraphenylbenzene-1,4-diylidene[bis(2-methyl-4,6-diisopropylindenyl)zirconium dichloride], 1,4-dihydro-1,4-disila-2,3,5,6-tetraphenylbenzene-1,4-diylidene[bis(2-methyl-4,5-benzoindenyl)zirconium dichloride], 1,4-dihydro-1,4-disila-2,3,5,6-tetraphenylbenzene-1,4-diylidene[bis(2-ethyl-4-phenylindenyl)zirconium dichloride], 1,4-dihydro-1,4-disila-2,3,5,6-tetraphenylbenzene-1,4-diylidene(bis(2-methyl-α-acenaphthindenyl)zirconium dichloride], 1,6-bis[methylsilyl-(2-methyl-4-phenylindenyl(2-methylindenyl)zirconium dichloride]hexane, 1,6-bis[methylsilyl-(2 -methyl-4-phenylindenyl(indenyl)zirconium dichloride]hexane, 1,6-bis[methylsilyl-(2-methyl-4-phenylindenyl)(2-methyl-4,5-benzoindenyl)zirconium dichloride]hexane, 1,6-bis[methylsilyl-(2-methyl-4-phenylindenyl)(2-methyl-4-(1-naphthyl)indenyl)zirconium dichloride]hexane, 1,6-bis[methylsilyl-(2-methyl-4-phenylindenyl)(2-methyl-4-isopropylindeny)zirconium dichloride]hexane, 1,6-bis[methylsilyl-(2-methyl-4-phenylindenyl)(2-methyl-4,6-diisopropylindenyl)zirconium dichloride]hexane, 1,6-bis[methylsilyl-(2-methyl-4-phenylindenyl)(2-ethylindenyl)zirconium dichloride]hexane, 1,6-bis[methylsilyl-(2-methyl-4-phenylindenyl)(2-ethyl-4-phenylindenyl)zirconium dichloride]hexane, 1,6-bis[methylsilyl-(2-methyl-4-phenylindenyl(2-methyl-α-acenaphthindenyl)zirconium dichloride]hexane.

1,2-bis(methylsilyl-(2-methyl-4-phenylindenyl)(indenyl)-zirconium dichloride]ethane, 1,2-bis[methylsilyl-(2-methyl-4-phenylindenyl)(2-methylindenyl)zirconium dichloride]ethane, 1,2-bis[methylsilyl-(2-methyl-4-phenylindenyl)(2-methyl-4,5-benzoindenyl)zirconium dichloride]ethane, 1,2-bis[methylsilyl-(2-methyl-4-phenylindenyl)(2-methyl-4,5-benzoindenyl)zirconium dichloride]ethane, 1,2-bis[methylsilyl-(2-methyl-4-phenylindenyl)(2-methyl-4-(1-naphthyl)indenylzirconium dichloride]ethane, 1,2-bis[methylsilyl-(2-methyl-4-phenylindenyl)(2-methyl-4-isopropylindenyl)zirconium dichloride]ethane, 1,2-bis[methylsilyl-(2-methyl-4-phenylindenyl)(2-methyl-4,6-diisopropylindenyl)zirconium dichloromethane, 1,2-bis[methylsilyl-(2-methyl-4-phenylindenyl)(2-ethylindenyl)zirconium dichloride]ethane, 1,2-bis[methylsilyl-(2-methyl-4-phenylindenyl)(2-ethyl-4-phenylindenyl)zirconium dichloride]ethane, 1,2-bis[methylsilyl-(2-methyl-4-phenylindenyl)(2-ethyl-4-(1-naphthyl)indenyl)zirconium dichloride]ethane, 1,2-bis[methylsilyl-(2-methyl-4-phenylindenyl)(2-methyl-α-acenaphthindenyl)zirconium dichloride]ethane, 1,4-disilacyclohexane-1,4-diylidene((2-methyl-4-phenylindenyl)(indenyl)zirconium dichloride], 1,4-disilacyclohexane-1,4-diylidene[(2-methyl-4-phenylindenyl)(2-methylindenyl)zirconium dichloride], 1,4-disilacyclohexane-1,4-diylidene[(2-methyl-4-phenylindenyl)(2-ethylindenyl)zirconium dichloride], 1,4-disilacyclohexane-1,4-diylidene[(2-methyl-4-phenylindenyl)(2-methyl-4-(1-naphthylindenyl)zirconium dichloride], 1,4-disilacyclohexane-1,4-diylidene[(2-methyl-4-phenylindenyl)(2-methyl-4-isopropylindenyl)zirconium dichloride], 1,4-dihydro-1,4-disilabenzene-1,4-diylidene[(2-methyl-4-phenylindenyl)(2-methyl-4-(1-naphthylindenyl)zirconium dichloride], 1,4-dihydro-1,4-disilabenzene-1,4-diylidene[(2-methyl-4-phenylindenyl)(2-methyl-4-isopropylindenyl)zirconium dichloride], 1,4-dihydro-1,4-disilabenzene-1,4-diylidene[(2-methyl-4-phenylindenyl)(2-methyl-4,6-diisopropylindenyl)zirconium dichloride], 1,4-dihydro-1,4-disilabenzene-1,4-diylidene[(2-methyl-4-phenylindenyl)(2-methyl-4,5-benzoindeny)zirconium dichloride], 1,4-dihydro-1,4-disilabenzene-1,4-diylidene[(2-methyl-4-phenylindenyl)(2-ethyl-4-phenylindenyl)zirconium dichloride] and 1,4-dihydro-1,4-disilabenzene-1,4-diylidene[(2-methyl-4-phenylindenyl)(2-methyl-α-acenaphthindenyl)zirconium dichloride].

12. The process as claimed in claim 1, wherein k is 2 and $B^1$ is

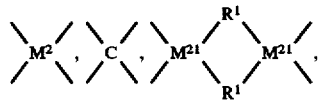

-continued

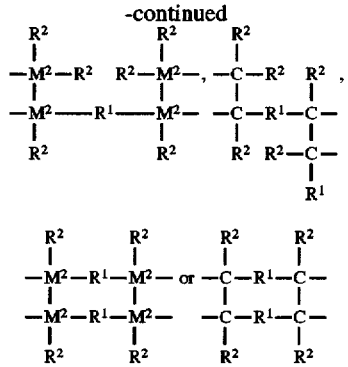

$M^{21}$ is germanium or tin.

13. The process as claimed in claim 12, wherein $B^1$ is

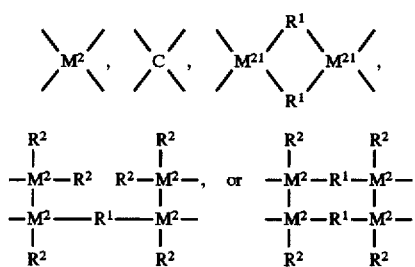

$M^{21}$ is germanium or tin.

14. The process as claimed in claim 1, wherein k is an integer greater than 2 and up to 100,000.

15. The process as claimed in claim 1, wherein k is an integer from 2 to 20 and $B^1$ is

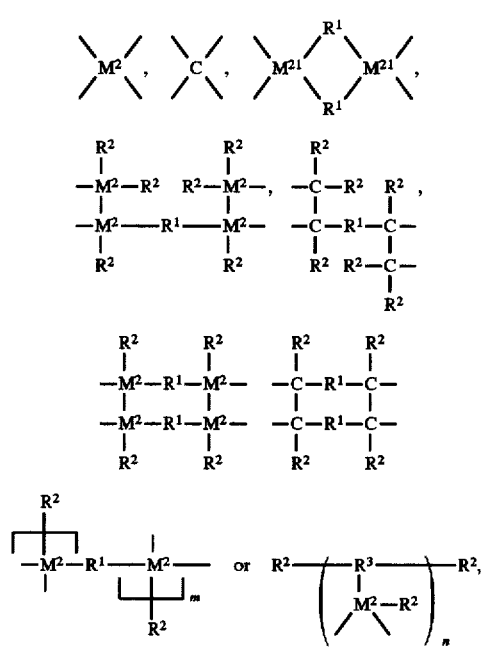

$M^{21}$ is germanium or tin.

16. The process as claimed in claim 1, wherein k is 2 and $B^1$ is

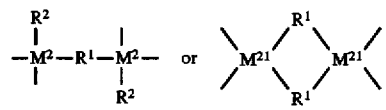

where $M^{21}$ is germanium or tin, $M^2$ is silicon, $R^1$ are identical or different and are a divalent linear or branched $C_1$–$C_6$-alkyl group and the radicals $R^2$ are identical or different and are a hydrogen or $C_1$–$C_4$ alkyl group or $C_6$–$C_{10}$ aryl group.

17. A process for preparing an olefin polymer by polymerization of at least one olefin in the presence of a catalyst which contains at least one polynuclear metallocene and at least one cocatalyst, wherein the polynuclear metallocene is of the formula II

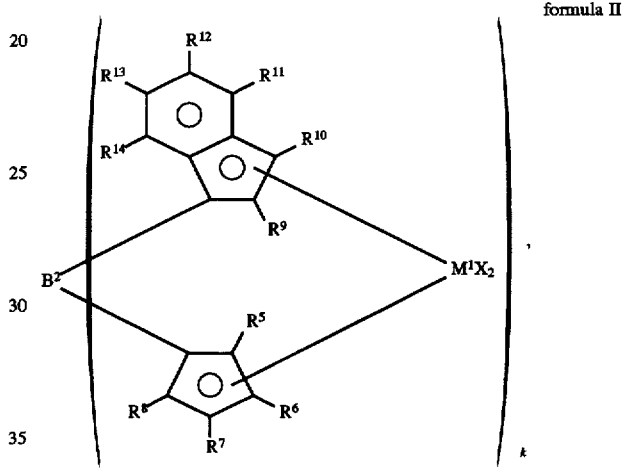

formula II where $M^1$ are identical or different and are a metal of group IVb, Vb or VIb of the Periodic Table, X are identical or different and are hydrogen, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-aryl-alkenyl group, an OH group, a halogen atom or pseudo-halogen, the radicals $R^5$, $R^6$, $R^7$ and $R^8$ are identical or different and are a hydrogen atom, a halogen atom, a $C_1$–$C_{10}$-alkyl group which can be halogenated, a $C_6$–$C_{20}$-aryl group, a $C_7$–$C_{40}$-arylalkyl group, a $C_7$–$C_{40}$-alkylaryl group, a $C_2$–$C_{10}$-alkenyl group, a $C_8$–$C_{40}$-arylalkenyl group, a $-NR^{15}_2$, $-SR^{15}$, $-OSiR^{15}_3$, $-SiR^{15}_3$ or $-PR^{15}_2$ radical, where $R^{15}$ is identical or different and is a $C_1$–$C_{10}$-alkyl group or a $C_6$–$C_{10}$-aryl group, or two or more adjacent radicals $R^5$, $R^6$, $R^7$ and $R^8$ together with the atoms connecting them form a ring system, $R^9$ to $R^{14}$ are identical or different and are a hydrogen atom, a halogen atom, a $C_1$–$C_{10}$-alkyl group which can be halogenated, a $C_6$–$C_{20}$-aryl group, a $C_7$–$C_{40}$-arylalkyl group, a $C_7$–$C_{40}$-alkylaryl group, a $C_2$–$C_{10}$-alkenyl group, a $C_8$–$C_{40}$-arylalkenyl group, a $-NR^{15}_2$, $-SR^{15}$, $-OSiR^{15}_3$, $-SiR^{15}_3$ or $-PR^{15}_2$ radical, where $R^{15}$ is identical or different and is a $C_1$–$C_{10}$-alkyl group or a $C_6$–$C_{10}$-aryl group, or two or more adjacent radicals $R^9$, $R^{10}$, $R^{11}$, $R^{12}$, $R^{13}$ and $R^{14}$ together with the atoms connecting them form a ring system, k is 2, if $B^1$ is

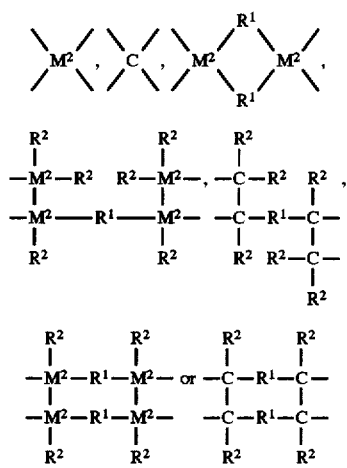

and k is an integer >2 if $B^1$ is

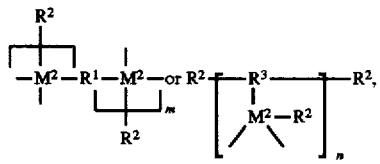

where $R^1$ are identical or different and are a divalent hydrocarbon-containing $C_1$–$C_{40}$ bridge structure, the radicals $R^2$ are identical or different and are a hydrogen atom, a halogen atom or a hydrocarbon-containing $C_1$–$C_{40}$ radical, $R^3$ is a trivalent hydrocarbon-containing $C_1$–$C_{40}$ radical, and n is k and m is k−1 and $M^2$ is silicon, germanium or tin.

18. The process as claimed in claim 17, wherein $M^1$ are identical or different and are zirconium or hafnium, the radicals X are identical and are a $C_1$–$C_4$-alkyl group, a $C_7$–$C_{10}$-alkylaryl group or a halogen atom, $R^5$ to $R^8$ are identical or different and are a hydrogen atom, a $C_1$–$C_{10}$-alkyl group, a $C_6$–$C_{20}$-aryl group or a $SiR^{15}_3$ radical, where $R^{15}$ is a $C_1$–$C_{10}$-alkyl group, or the radicals $R^5$ and $R^6$ and/or $R^7$ and $R^8$ together with the atoms connecting them form an aromatic or aliphatic ring system, $R^9$ to $R^{14}$ are identical or different and are a hydrogen atom, a $C_1$–$C_{10}$-alkyl group or a $C_6$–$C_{20}$-aryl group, or $R^9$ and R and/or two or more adjacent radicals $R^{11}$, $R^{12}$, $R^{13}$ and $R^{14}$ together with the atoms connecting them form an aromatic or aliphatic ring system, k is 2,
B is

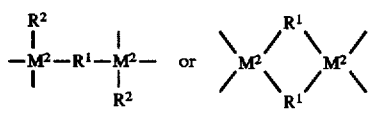

where $M^2$ is silicon, $R^1$ are identical or different and are a divalent linear or branched $C_1$–$C_6$-alkyl group, and the radicals $R^2$ are identical or different and are hydrogen, a $C_1$–$C_4$-alkyl group or a $C_6$–$C_{10}$-aryl group.

19. The process as claimed in claim 18, wherein said at least one cocatalyst is supported and/or prepolymerized.

20. The process as claimed in claim 17, wherein k is 2 and $B^1$ is

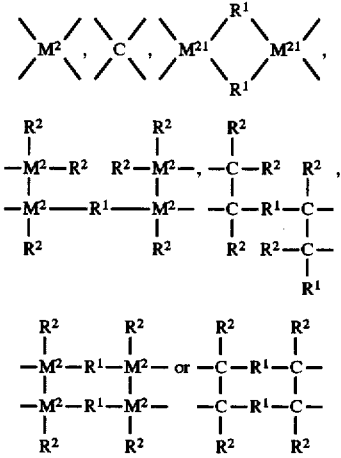

$M^{21}$ is germanium or tin.

21. The process as claimed in claim 20, wherein $B^1$ is

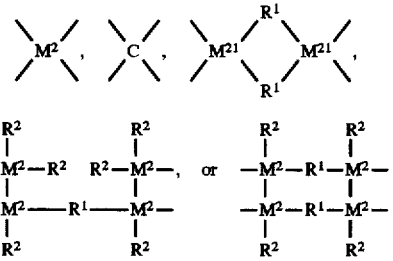

$M^{21}$ is germanium or tin.

22. The process as claimed in claim 17, wherein k is an integer greater than 2 and up to 100,000.

23. The process as claimed in claim 17, wherein k is an integer from 2 to 20 and $B^1$ is

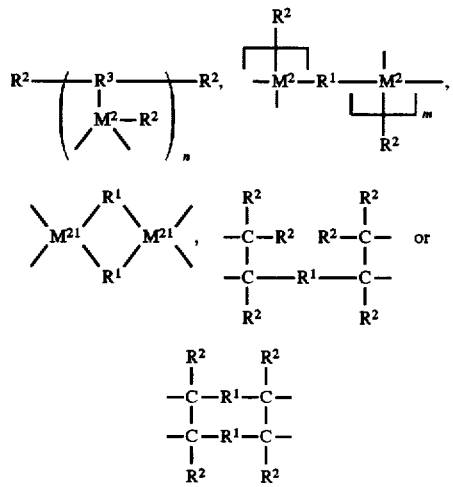

$M^{21}$ is germanium or tin.

24. The process as claimed in claim 17, wherein k is 2 and $B^1$ is

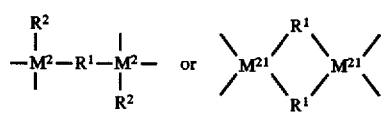
where $M^{21}$ is germanium or tin,
$M^2$ is silicon,
$R^1$ are identical or different and are a divalent linear or branched $C_1$–$C_6$-alkyl group and the radicals $R^2$ are identical or different and are a hydrogen or $C_1$–$C_4$ alkyl group or $C_6$–$C_{10}$ aryl group.
* * * * *